(12) United States Patent
Solomon et al.

(10) Patent No.: US 8,523,831 B2
(45) Date of Patent: Sep. 3, 2013

(54) DISINFECTING CAPS HAVING SEALING FEATURES AND RELATED SYSTEMS AND METHODS

(75) Inventors: Donald D. Solomon, North Salt Lake, UT (US); Steven Bandis, West Jordan, UT (US); James Mercer, West Jordan, UT (US); Michael Howlett, Salt Lake City, UT (US); Robert Hitchcock, Sandy, UT (US); James Kennedy, Salt Lake City, UT (US); Richard Lasher, Salt Lake City, UT (US)

(73) Assignees: Catheter Connections, Inc., Salt Lake City, UT (US); The University of Utah Research Foundation, Salt Lake City, UT (US)

( * ) Notice: Subject to any disclaimer, the term of this patent is extended or adjusted under 35 U.S.C. 154(b) by 132 days.

(21) Appl. No.: 12/957,263

(22) Filed: Nov. 30, 2010

(65) Prior Publication Data

US 2011/0213341 A1   Sep. 1, 2011

Related U.S. Application Data

(63) Continuation-in-part of application No. 12/917,336, filed on Nov. 1, 2010, which is a continuation-in-part of application No. 12/610,141, filed on Oct. 30, 2009, now Pat. No. 8,172,825.

(60) Provisional application No. 61/265,216, filed on Nov. 30, 2009.

(51) Int. Cl.
*A61M 5/14* (2006.01)
*A61M 39/00* (2006.01)
*B65D 43/03* (2006.01)
*A01N 25/00* (2006.01)

(52) U.S. Cl.
USPC ........... 604/256; 604/533; 604/905; 424/405; 220/380

(58) Field of Classification Search
USPC ................... 604/905, 29, 283, 256, 403, 533; 424/292, 28, 405; 220/380
See application file for complete search history.

(56) References Cited

U.S. PATENT DOCUMENTS

| 2,351,804 A | 6/1944 | Bium |
| 3,446,596 A | 5/1969 | Salivar et al. |

(Continued)

FOREIGN PATENT DOCUMENTS

| WO | WO-2006/099306 | 9/2006 |
| WO | WO-2008/089196 | 7/2008 |

(Continued)

OTHER PUBLICATIONS

Final Office Action mailed Apr. 22, 2011 in co-pending U.S. Appl. No. 12/164,310, now published as U.S. Publication No. US-2009/0008393.

(Continued)

*Primary Examiner* — Kevin C Sirmons
*Assistant Examiner* — William Carpenter
(74) *Attorney, Agent, or Firm* — Sunstein Kann Murphy & Timbers LLP

(57) ABSTRACT

Caps can be used to cover and disinfect medical connectors. Some caps can create a seal with the medical connectors to prevent antiseptic from entering a fluid paths defined by a connector. Support members can aid in creating or maintaining the seal.

21 Claims, 30 Drawing Sheets

(56) References Cited

U.S. PATENT DOCUMENTS

| | | | |
|---|---|---|---|
| 3,987,930 A * | 10/1976 | Fuson | 220/287 |
| 4,232,677 A | 11/1980 | Leibinsohn | |
| 4,324,239 A | 4/1982 | Gordon et al. | |
| 4,340,052 A | 7/1982 | Dennehey et al. | |
| 4,346,703 A | 8/1982 | Dennehey et al. | |
| 4,354,490 A | 10/1982 | Rogers | |
| 4,369,781 A | 1/1983 | Gilson et al. | |
| 4,402,691 A | 9/1983 | Rosenthal et al. | |
| 4,432,764 A | 2/1984 | Lopez | |
| 4,432,766 A | 2/1984 | Bellotti et al. | |
| 4,440,207 A | 4/1984 | Genatempo et al. | |
| 4,450,624 A | 5/1984 | Collier | |
| 4,671,306 A | 6/1987 | Spector | 132/73 |
| 4,778,447 A * | 10/1988 | Velde et al. | 604/29 |
| 4,838,875 A | 6/1989 | Somor | |
| 5,205,821 A | 4/1993 | Kruger et al. | |
| 5,242,425 A | 9/1993 | White et al. | |
| 5,385,372 A * | 1/1995 | Utterberg | 285/332 |
| 5,466,219 A | 11/1995 | Lynn et al. | |
| 5,554,135 A | 9/1996 | Menyhay | |
| 5,694,978 A | 12/1997 | Heilmann et al. | |
| 5,792,120 A | 8/1998 | Menyhay | |
| 5,894,015 A | 4/1999 | Rechtin | |
| 5,951,519 A | 9/1999 | Utterberg | |
| 5,954,957 A | 9/1999 | Chin-Loy et al. | 210/232 |
| 6,045,539 A | 4/2000 | Menyhay | |
| 6,171,287 B1 | 1/2001 | Lynn et al. | |
| 6,932,795 B2 | 8/2005 | Lopez et al. | |
| 6,960,191 B2 | 11/2005 | Howlett et al. | |
| 7,040,598 B2 | 5/2006 | Raybuck | |
| 7,198,611 B2 | 4/2007 | Connell et al. | |
| D547,446 S | 7/2007 | Racz et al. | |
| D550,355 S | 9/2007 | Racz et al. | |
| 7,316,669 B2 | 1/2008 | Ranalletta | |
| D607,325 S | 1/2010 | Rogers et al. | |
| 7,762,524 B2 | 7/2010 | Cawthon et al. | |
| 7,780,794 B2 | 8/2010 | Rogers et al. | |
| 7,922,701 B2 | 4/2011 | Buchman | 604/256 |
| 7,985,302 B2 | 7/2011 | Rogers et al. | |
| 2002/0093192 A1 | 7/2002 | Matkovich | |
| 2003/0140441 A1 | 7/2003 | Stafford | |
| 2003/0153865 A1 | 8/2003 | Connell et al. | |
| 2003/0198502 A1 | 10/2003 | Maloney et al. | |
| 2004/0039341 A1 | 2/2004 | Ranalletta | 604/199 |
| 2004/0201216 A1 | 10/2004 | Segal et al. | |
| 2004/0214316 A1 | 10/2004 | O'Connell | |
| 2004/0258560 A1 | 12/2004 | Lake, Jr. et al. | 422/28 |
| 2005/0033267 A1 | 2/2005 | Decaria | |
| 2005/0124970 A1 | 6/2005 | Kunin et al. | |
| 2005/0147524 A1 | 7/2005 | Bousquet | 422/28 |
| 2005/0203460 A1 | 9/2005 | Kim | |
| 2005/0245883 A1 | 11/2005 | Baldwin | |
| 2005/0266714 A1 | 12/2005 | Higgins et al. | |
| 2006/0030827 A1 | 2/2006 | Raulerson et al. | |
| 2007/0112333 A1* | 5/2007 | Hoang et al. | 604/533 |
| 2007/0202177 A1 | 8/2007 | Hoang | |
| 2007/0287989 A1 | 12/2007 | Crawford et al. | |
| 2007/0293818 A1 | 12/2007 | Stout et al. | |
| 2007/0293822 A1 | 12/2007 | Crawford et al. | |
| 2008/0021381 A1 | 1/2008 | Lurvey et al. | |
| 2008/0027399 A1 | 1/2008 | Harding et al. | |
| 2008/0038167 A1 | 2/2008 | Lynn | |
| 2008/0039803 A1 | 2/2008 | Lynn | |
| 2008/0086091 A1 | 4/2008 | Anderson et al. | |
| 2008/0095680 A1 | 4/2008 | Steffens et al. | |
| 2008/0105704 A1 | 5/2008 | Pritchard | |
| 2008/0107564 A1 | 5/2008 | Sternberg et al. | |
| 2008/0132880 A1 | 6/2008 | Buchman | |
| 2008/0147047 A1 | 6/2008 | Davis et al. | |
| 2008/0177250 A1 | 7/2008 | Howlett et al. | |
| 2008/0235888 A1 | 10/2008 | Vaillancourt et al. | |
| 2009/0008393 A1 | 1/2009 | Howlett et al. | |
| 2009/0062766 A1 | 3/2009 | Howlett et al. | |
| 2009/0205151 A1* | 8/2009 | Fisher et al. | 15/104.04 |
| 2010/0047123 A1 | 2/2010 | Solomon et al. | |
| 2010/0049170 A1 | 2/2010 | Solomon et al. | |
| 2010/0242993 A1 | 9/2010 | Hoang et al. | |
| 2010/0306938 A1 | 12/2010 | Rogers et al. | |
| 2010/0313366 A1 | 12/2010 | Rogers et al. | |
| 2011/0044850 A1 | 2/2011 | Solomon et al. | 422/28 |
| 2011/0217212 A1 | 9/2011 | Solomon et al. | |

FOREIGN PATENT DOCUMENTS

| | | |
|---|---|---|
| WO | WO-2008/100950 | 8/2008 |
| WO | WO-2010/002808 | 1/2010 |
| WO | WO-2010/141508 | 12/2010 |
| WO | WO-2011/053924 | 5/2011 |
| WO | WO-2011/066565 | 6/2011 |
| WO | WO-2011/066586 | 6/2011 |

OTHER PUBLICATIONS

Response to Requirement for Election of Species filed Apr. 1, 2011 in co-pending U.S. Appl. No. 12/171,997, now published as U.S. Publication No. US-2009/0062766.

Office Action mailed Jun. 9, 2011 in co-pending U.S. Appl. No. 12/171,997, now published as U.S. Publication No. US-2009/0062766.

Preliminary Amendment filed Jun. 13, 2011 in co-pending U.S. Appl. No. 29/383,403.

Preliminary Amendment filed May 13, 2011 in co-pending U.S. Appl. No. 12/956,704.

Maki, Dennis G., "In Vitro Studies of a Novel Antimicrobial Luer-Activated Needleless Connector for Prevention of Catheter-Related Blookstream Infection," Clinical Infection Diseases, Jun. 15 2010, vol. 50, Issue 12, pp. 1580-1587.

Curos Port Protector web page from hitp://www.iveramed.com./, dated Jul. 11, 2008.

Curos Port Protector product brochure, circa Nov. 2008, http://www.iveramed.com/docs/Curos%20Brochure-FINAL.pdf.

Hospira Male/Female Sterile Cap product packaging insert and brochure, circa Aug. 2004.

BD Q-Syte Luer Access Split Septum product brochure, circa Nov. 2008, http://www.bd.com/infusion/pdfs/D16333.pdf.

Tego Connector product brochure, circa Nov. 2008, http://www.icumed.com/Docs-Tego/M1-1148%20TEGO%20Folder%20Brochure%20Rev.3.pdf.

Baxa Corporation Launches PadLock Set Saver for IV Safety press release, Oct. 10, 2007 http://www.pr.com/press-release/555432.

Baxa Corporation PadLock Set Saver Specifications and Instructions for Use, Copyright 2007, http://www.baxa.com/resources/docs/5300103905C.pdf.

Baxa Corporation Padlock product brochure, Copyright 2007, http://www.baxa.com/resources/docs/5300104405A.pdf.

Baxa Corporation Padlock Microbial Testing Technical Paper, Copyright 2007, http://www.baxa.com/resources/docs/technicalPaper/PadlockMicrobialChallengeTechPaper.pdf.

Baxa Corporation Padlock catalog page, Copyright 2009, http://www.baxa.com/SearchResults/ProductDetail/?id=6452BFB9-3048-7B87-701697FB93902BA6.

One Less Problem, Managing Infection Control, Jun. 2008, http://www.baxa.com/resourcces/docs/OneLessProbPaper.pdf.

Unomedical Medical Products catalog, circa Jan. 2006, http://www.unomedical.net/au/section05/section10/LocalSSI/..%5C..%5Cpdf%5Cmedical.pdf.

Braum product catalog, circa Aug. 2008.

Buchman, et al., "A New Central Venous Catheter Cap: Decreased Microbial Growth and Risk for Catheter-Related Bloodstream Infection," The Journal of Vascular Access 2009, 10: pp. 11-21.

Restriction Requirement mailed Nov. 13, 2008 in U.S. Appl. No. 12/014,388, now abandoned.

Amendment and Response to Restriction Requirement filed Mar. 24, 3009 in U.S. Appl. No. 12/014,388, now abandoned.

Interview Summary mailed Sep. 1, 2009 in U.S. Appl. No. 12/014,388, now abandoned.

Office Action mailed May 5, 2009 in U.S. Appl. No. 12/014,388, now abandoned.

Amendment and Response to Office Action filed Sep. 4, 2009 in U.S. Appl. No. 12/014,388, now abandoned.

Notice of Non-Compliance Amendment mailed Sep. 28, 2009 in U.S. Appl. No. 12/014,388, now abandoned.
Amendment and Response to Office Action filed Oct. 2, 2009 in U.S. Appl. No. 12/014,388, now abandoned.
Final Office Action mailed Jan. 27, 2010 in U.S. Appl. No. 12/014,388, now abandoned.
RCE and Amendment and Response to Office Action filed Apr. 26, 2010 in U.S. Appl. No. 12/014,388, now abandoned.
Office Action mailed Jun. 21, 2010 in U.S. Appl. No. 12/014,388, now abandoned.
Amendment and Response to Office Action filed Oct. 19, 2010 in U.S. Appl. No. 12/014,388, now abandoned.
Interview Summary mailed Oct. 25, 2010 in U.S. Appl. No. 12/014,388, now abandoned.
Final Office Action mailed Dec. 23, 2010 in U.S. Appl. No. 12/014,388, now abandoned.
Express Abandonment filed Feb. 15, 2011 in U.S. Appl. No. 12/014,388, now abandoned.
Restriction Requirement mailed May 21, 2010 in co-pending U.S. Appl. No. 12/164,310, now published as US 2009/0008393.
Amendment and Response to Restriction Requirement filed Jun. 21, 2010 in co-pending U.S. Appl. No. 12/164,310, now published as US 2009/0008393.
Office Action mailed Aug. 16, 2010 in co-pending U.S. Appl. No. 12/164,310, now published as US 2009/0008393.
Amendment and Response to Office Action filed Oct. 29, 2010 in co-pending U.S. Appl. No. 12/164,310, now published as US 2009/0008393.
Interview Summary mailed Oct. 25, 2010 in co-pending U.S. Appl. No. 12/164,310, now published as US 2009/0008393.
Notice of Non-Compliant Amendment mailed Nov. 3, 2010 in co-pending U.S. Appl. No. 12/164,310, now published as US 2009/0008393.
Amendment and Response to Office Action filed Feb. 16, 2011 in co-pending U.S. Appl. No. 12/164,310, now published as US 2009/0008393.
Preliminary Amendment filed Dec. 7, 2010 in co-pending U.S. Appl. No. 12/171,997, now published as US 2009/0062766.
Restriction Requirement mailed Dec. 9, 2010 in co-pending U.S. Appl. No. 12/171,997, now published as US 2009/0062766.
Notification of Transmittal of the International Search Report and the Written Opinion of the International Searching Authority issued Aug. 1, 2008 in International Application No. PCT/US2008/051087.
Notification of Transmittal of the International Search Report and the Written Opinion of the International Searching Authority issued Aug. 31, 2009 in International Application No. PCT/US2009/049094.
Notification of Transmittal of the International Search Report and the Written Opinion of the International Searching Authority issued Jan. 6, 2011 in International Application No. PCT/US2010/054995.
Notification of Transmittal of the International Search Report and the Written Opinion of the International Searching Authority issued Jan. 26, 2011 in International Application No. PCT/US2010/058404.
Notification of Transmittal of the International Search Report and the Written Opinion of the International Searching Authority issued Feb. 7, 2011 in International Application No. PCT/US2010/058453.
Co-pending U.S. Appl. No. 12/917,336 titled Disinfecting Caps and Systems and Associated Methods, filed Nov. 1, 2010.
Co-pending Design U.S. Appl. No. 29/383,403 titled Capping System for Use With One or More Medical Connectors, filed Jan. 17, 2011.
Co-pending U.S. Appl. No. 12/956,704 titled Disinfecting Caps Having an Extendable Feature and Related Systems and Methods, filed Nov. 30, 2010.

* cited by examiner

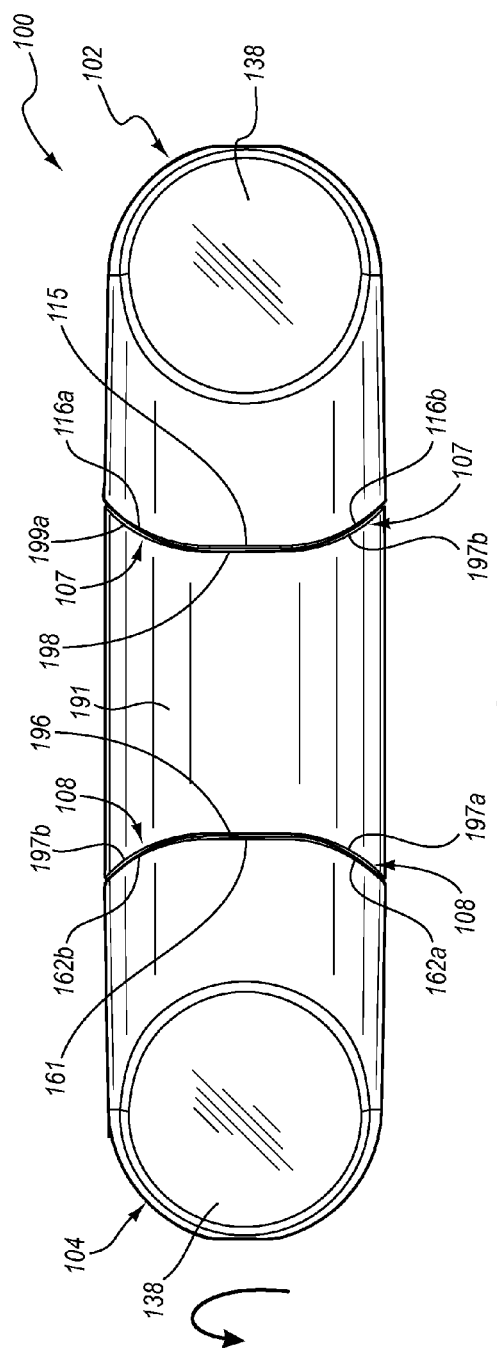
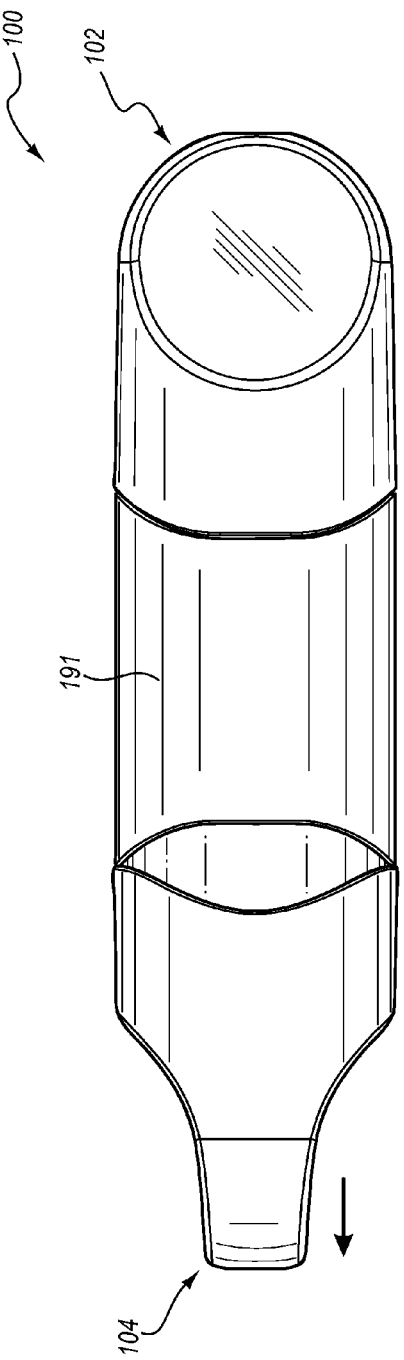
FIG. 7A
FIG. 7B

DISINFECTING CAPS HAVING SEALING FEATURES AND RELATED SYSTEMS AND METHODS

CROSS-REFERENCE TO RELATED APPLICATIONS

This application claims the benefit of U.S. Provisional Patent Application No. 61/265,216, titled STERILIZATION CAPS AND SYSTEMS AND ASSOCIATED METHODS, filed Nov. 30, 2009; and this application is a continuation-in-part of U.S. patent application Ser. No. 12/917,336, titled DISINFECTING CAPS AND SYSTEMS AND ASSOCIATED METHODS, filed Nov. 1, 2010, which is a continuation-in-part of U.S. patent application Ser. No. 12/610,141, titled STERILIZATION CAPS AND SYSTEMS AND ASSOCIATED METHODS, filed Oct. 30, 2009, the entire contents of each of which are hereby incorporated by reference herein. The earliest date to which this application claims priority is Oct. 30, 2009.

BACKGROUND

1. Technical Field

The present disclosure generally relates to caps for medical connectors and more specifically relates to caps that can be used to protect the cleanliness of unconnected medical connectors, such as connectors that may be used for fluid flow or for fluid delivery systems. Some embodiments are directed to caps for medical connectors that include male-type interfaces and/or medical connectors that include female-type interfaces.

2. Related Art

Bloodstream infections, such as may be caused by microorganisms that enter patients via intravascular catheters, are a significant cause of illness and excess medical costs. A substantial number of such infections occur in U.S. intensive care units annually. Additionally, a significant fraction of these infections result in death.

Guidelines from the Centers for Disease Control and Prevention describe various ways to limit bloodstream infections in hospital, outpatient, and home care settings. The guidelines address issues such as hand hygiene, catheter site care, and admixture preparation. However, despite these guidelines, such infections continue to plague healthcare systems at relatively unchanged rates.

Impregnating catheters with various antimicrobial agents is one approach for reducing these infections. Impregnated catheters, however, provide less than satisfactory results. Additionally, some microbes have developed resistance to the various antimicrobial agents used in the catheters. Other systems and approaches have also been developed, but these likewise suffer from a variety of limitations and drawbacks.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 7A is a top plan view of the assembly of FIG. 1;

FIG. 7B is a top plan view of the assembly of FIG. 1 showing a male cap portion thereof having been rotated so as to assist in the release of the male cap from the assembly;

DETAILED DESCRIPTION

Disclosed herein are disinfecting caps, and related systems and methods, that can protect and/or disinfect medical connectors. The caps, systems, and methods can reduce the threat of microorganisms entering the bloodstream of a patient via fluid flow or fluid delivery systems, such as, for example, stopcocks, female luer lock connectors, or other connectors having female-type interfaces. The disinfecting caps can be included in systems or assemblies that include additional caps (e.g., male caps), which may be used with connectors having male-type interfaces, such as fluid transfer devices having an elongated male portion or male protrusion. For example, the caps may be configured for use with a male luer connector. In some embodiments, a cap can be configured to couple with and disinfect a medical connector having an open conduit or lumen, which may be shaped substantially frustoconically, cylindrically, or in any other suitable shape. The female cap can include a sealing member that is configured to plug or seal the open conduit. In further embodiments, the cap can include an antiseptic, and can be configured to dispense the antiseptic after the open conduit has been sealed so as prevent antiseptic from entering the conduit, or more generally, from entering a fluid line. In some embodiments, the antiseptic may be contained within a pad prior to the coupling of the cap to the medical connector, and the act of coupling the cap to the medical connector can force at least a portion of the antiseptic from the pad and into contact with unsealed portions of the female connector. Caps may also be used to seal a fluid pathway of a male connector so as to prevent antiseptic from entering the fluid path.

Figure 1:
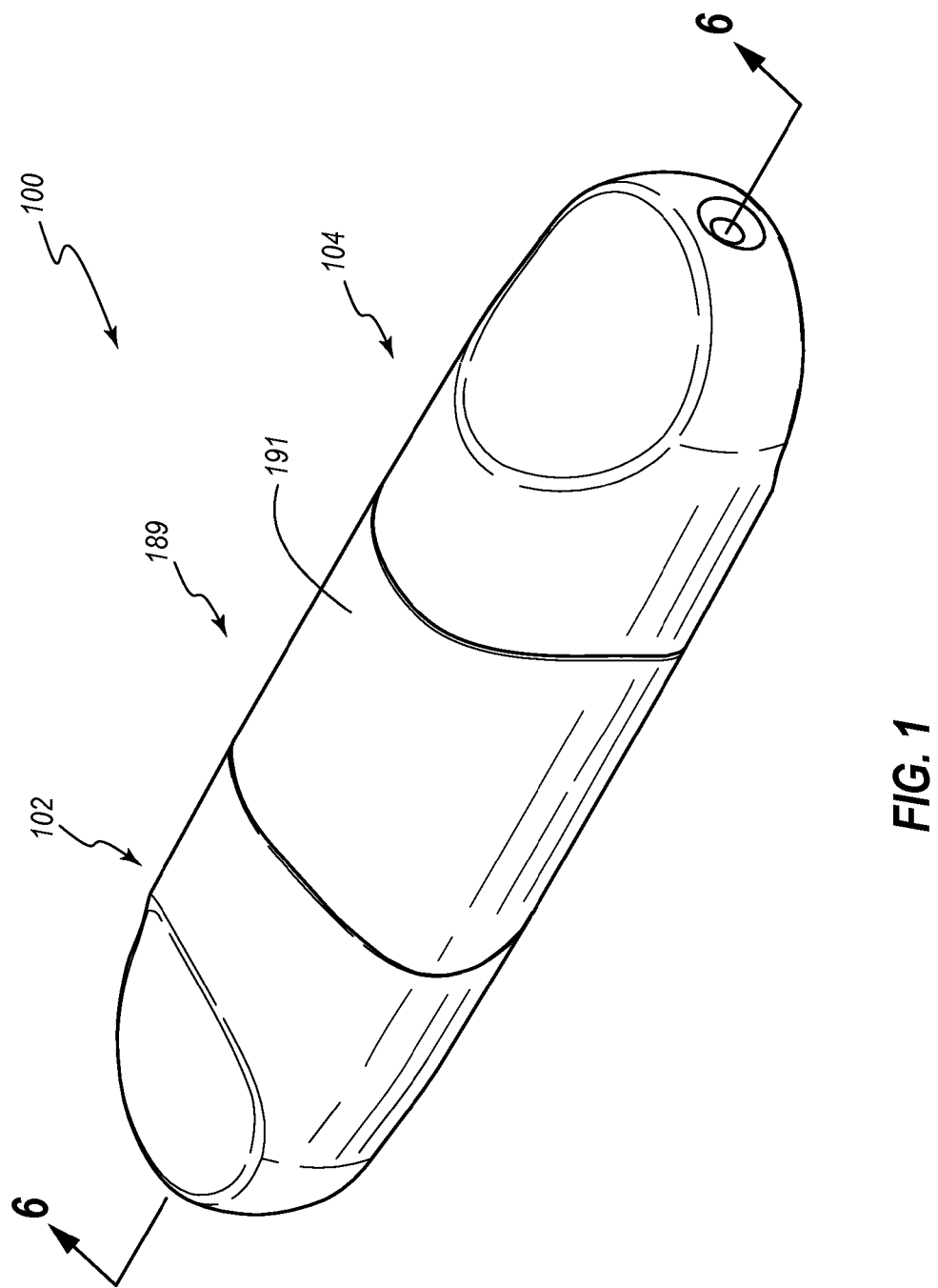
FIG. 1 is a perspective view of an embodiment of an assembly that includes an embodiment of a female cap and an embodiment of a male cap, which can be connected in a pre-use configuration via a sleeve.
Figure 2:
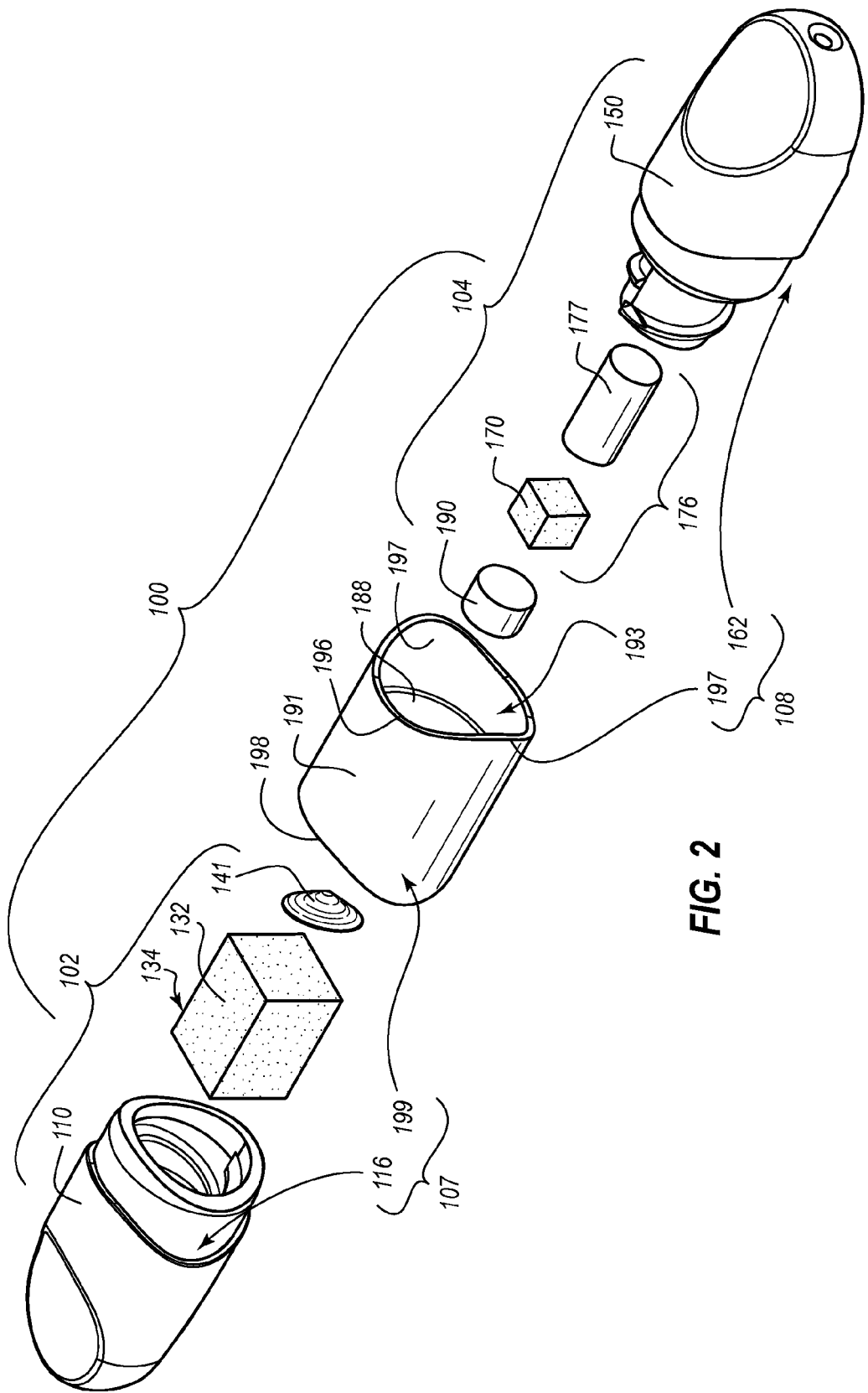
FIG. 2 is an exploded perspective view of the assembly of FIG. 1.
Figure 3:
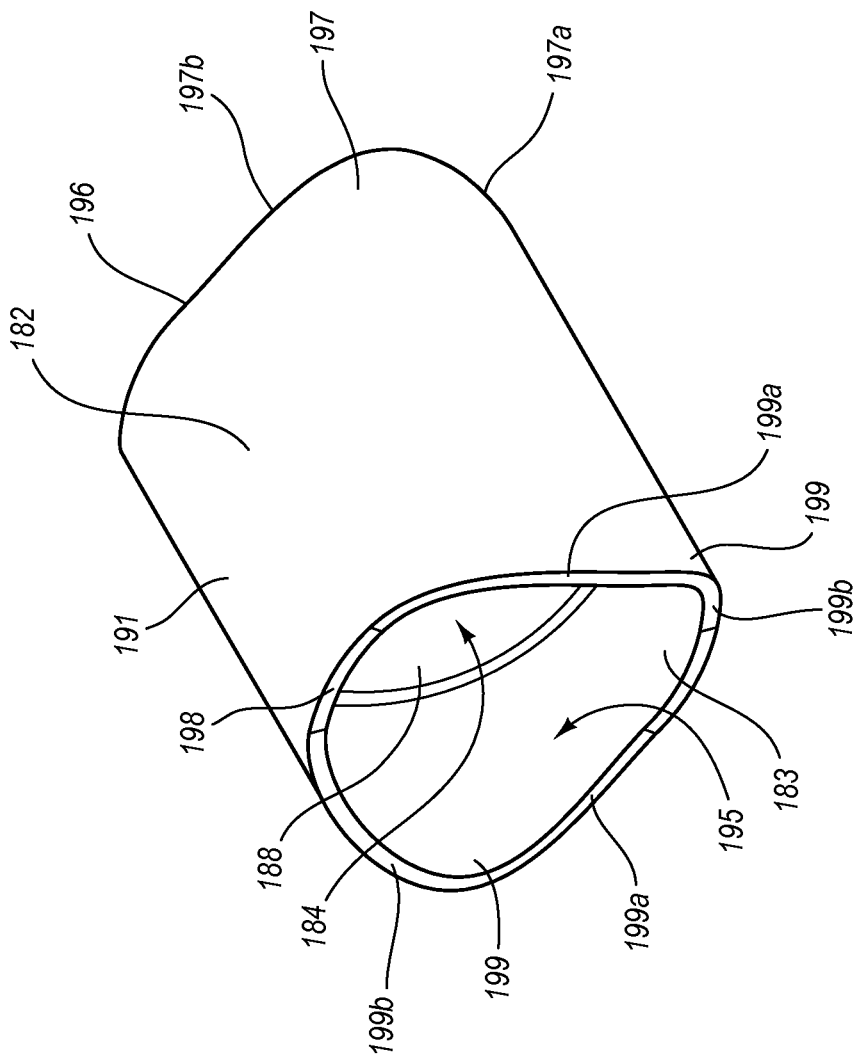
FIG. 3 is a perspective view of an embodiment of a sleeve that is compatible with the assembly of FIG. 1.

FIGS. 1-3 illustrate an embodiment of an assembly 100 that can include a female cap 102 and a male cap 104, each of which can be used to cover a separate medical connector. The assembly 100 can be provided in a pre-use, assembled, or closed state, and the caps 102, 104 can be removed from each other. In particular, the female and male caps 102, 104 can be coupled with each other via a sealing mechanism 189. In the illustrated embodiment, the sealing mechanism 189 comprises a sealing sleeve 191. The terms "coupled" and variants thereof are used in their ordinary sense and include arrangements in which the caps 102, 104 directly engage one another when the assembly 100 is in the assembled or pre-use state. The terms also include arrangements such as that illustrated in FIG. 1, where the caps 102, 104 do not directly contact one another when the assembly 100 is in the assembled or pre-use state, yet are securely held in a fixed relationship relative to one another. Stated otherwise, each of the caps 102, 104 is separately secured to the sealing sleeve 191, and thus, although the caps 102, 104 are spaced from one another, they nevertheless are coupled or indirectly secured to each other.

FIG. 2 is an exploded view of the assembly 100. The female cap 102 can include a housing 110 into which a support member 134 and a sealing member 141 are received. As discussed further below, the support member 134 can assist the sealing member 141 in the formation of a seal with a lumen of a female-type medical connector. For example, in some embodiments, the support member 134 can resist distal movement of the sealing member 141 within the housing 110. In further embodiments, the support member 134 may be resiliently deformable, and thus may urge the sealing member 141 in a proximal direction, such as in reaction to a distal movement of the sealing member 141. Accordingly, in some instances, the support member 134 may also be referred to as a biasing member. In the illustrated embodiment, the support member 134 comprises an antiseptic reservoir or pad 132, which is also discussed further below.

The male cap 104 can include a housing 150 into which a support or post 177, an antiseptic reservoir or pad 170, and a sealing member 190 are received. As further discussed below, the post 177 and the pad 170 may be considered as a multi-part support member 176 that is configured to resist movement of the sealing member 190 in a distal direction within the housing 150. In further embodiments, one or more of the post 177 and the pad 170 may be resiliently deformable (e.g., elastomeric) such that one or more of the post 177 and the pad 170 can urge the sealing member 190 toward a proximal end of the male cap 104, such as after the sealing member 190 has been displaced distally within the housing 150. Accordingly, in some instances, the support member 176 may also be referred to as a biasing member.

The terms "proximal" and "distal," when used herein relative to a cap, or components thereof, are used relative to the coupling of the cap with a medical device, such that the medical device is inserted into a proximal end of the cap, or component thereof and advanced toward a distal end of the cap or component. Accordingly, in the illustrated embodiment, the proximal ends of the caps 102, 104 are directed toward each other and the distal ends of the caps 102, 104 are directed away from each other when the assembly 100 is in the pre-use configuration (see FIG. 1). The female cap 102 can define one or more recesses 116 and the male cap 104 can define one or more recesses 162 at positions that are between the proximal and distal ends of the caps 102, 104, respectively.

The sleeve 191 can include end surfaces or edges 196, 198 that are configured to interact with the male and female caps 104, 102, respectively. The sleeve 191 can define one or more protrusions 199 that are configured to be received in the one or more recesses 116 of the female cap 102. Each protrusion 199/recess 116 pair can cooperate as a decoupling feature, release mechanism, or separation assist 107. Similarly, the sleeve 191 can define one or more protrusions 197 that are configured to be received in the one or more recesses 162 of the male cap 104. Each protrusion 197/recess 162 pair can cooperate as a separation assist 108. The protrusions 197, 199 and recesses 116, 162 can have rounded edges (e.g., rounded or radiused valleys and apexes), which can facilitate their rotational movement relative to one another.

As shown in FIG. 3, each protrusion 199 can include a portion of the edge 198 of the sleeve 191. Moreover, each protrusion 199 can define a pair of faces 199a, 199b that are angled in opposite directions. Here, the term "angled" refers to any suitable non-zero, non-180-degree angle relative to a transverse cross-sectional plane (not shown) that passes perpendicularly through a central axis of the sleeve 191. For a path that is traced along the edge 198 in a clockwise direction (when looking toward the edge 198), the path moves away from the longitudinal center of the sleeve 191 along the faces 199a, and the path moves toward the longitudinal center of the sleeve 191 along the faces 199b.

Similarly, each protrusion 197 can include a portion of the edge 196 of the sleeve 191, and each protrusion 197 can define a pair of oppositely angled faces 197a, 197b. For a path that is traced along the edge 196 in a clockwise direction (when looking toward the edge 196), the path moves away from the longitudinal center of the sleeve 191 along the faces 197a, and the path moves toward the longitudinal center of the sleeve along the faces 197b.

The protrusions 197, 199 can be relatively flexible, as they extend a greater distance from the longitudinal center of the sleeve 191, and thus define longer moment arms relative thereto. In some embodiments, the sleeve 191 includes a central band or reinforcing rib 188 that can provide structural integrity to the sleeve 191 and can prevent or inhibit large deformations of the sleeve 191 during use and/or crushing of the sleeve 191 after removal of one or more of the caps 102, 104 therefrom. The illustrated reinforcing rib 188 projects radially inwardly at a central region of the sleeve 191. In other embodiments, the reinforcing rib 188 may extend outwardly or may be omitted. For example, in some embodiments, the sleeve 191 may define a uniform thickness along its full length.

The sleeve 191 defines an external surface 182 and an internal surface 183, each of which extends away from the edges 196, 198. The internal surface 183 can define a cavity, opening, or lumen 184 into which proximal ends of the male and female caps 104, 102 can be received. The terms "external surface" and "internal surface" are used relative to the assembly 100 when it is in the pre-use state (e.g., the configuration shown in FIG. 1). Accordingly, when the assembly 100 is in an assembled state, the internal surface 183 is at an interior of the assembly 100, so as not to be exposed to an environment that surrounds the assembly 100, and the external surface 183 is at an exterior of the assembly, such that it is exposed to the environment and may be grasped or otherwise contacted by a user. It is noted that in the foregoing portion of the present specification, the terms "interior" and "exterior" may at times be used with respect to inwardly directed surfaces and outwardly directed surfaces of certain caps, without regard to whether any portion of these surfaces is in fact internal to an assembly that includes these caps when the assembly is in the pre-use state. The internal surface 183 of the sleeve 191 also can define a connection interface 193 (FIG. 3) and a connection interface 195 by which the caps 104, 102, respectively, can be coupled to the sleeve 191, as discussed further below.

With reference to FIGS. 4A-4C and 6, the housing 110 of the female cap 102 can extend between a closed distal end and an open proximal end. The closed distal end does not permit any fluid flow therethrough and serves as a barrier between an interior of the housing 110 and an exterior environment. The open proximal end of the housing 110 is configured to receive at least a portion of a medical connector therein. As discussed further below (e.g., with respect to FIG. 9), certain of such medical connectors can define an internal female lumen, which may at least partially define a fluid line or fluid delivery pathway. The connectors may have outwardly disposed threading or some other suitable connection interfacing, and the housing 110 may be sized to fit over, or about an outside of, such an arrangement. The housing 110 can include a sidewall 112, which defines the open proximal end, and a base wall 113, which defines at least a portion of the closed distal end.

The housing 110 can include a body region 136 near a proximal end thereof, which is substantially cylindrically shaped in the illustrated embodiment. A handle 137 can extend from the body region 136 so as to be positioned at the distal end of the cap 102. The handle 137 can comprise any suitable gripping features 103, which in illustrated embodiment comprise opposing gripping regions or grasping platforms 138 that are configured to provide a convenient surface against which a user can press so as to hold and/or twist the cap 102.

Figure 4C:
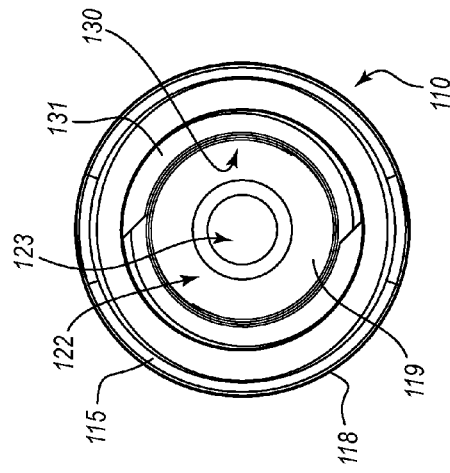
FIG. 4C is a front elevation view of the housing portion of the female cap of FIG. 4A.
Figure 4A:
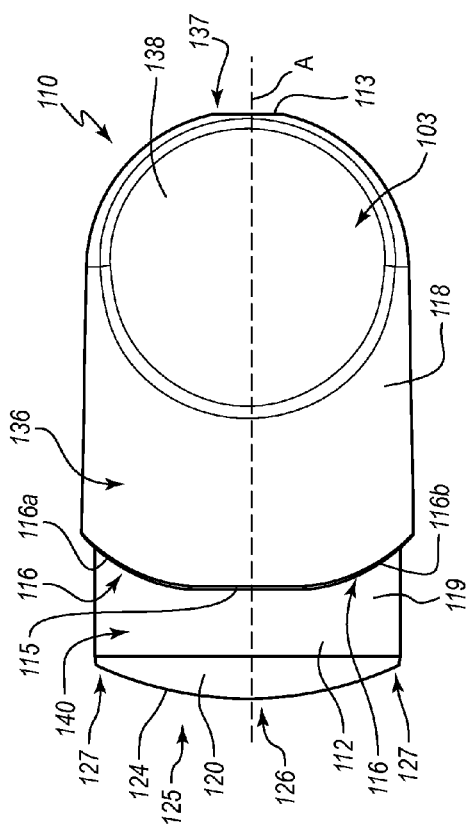
FIG. 4A is a top plan view of an embodiment of a housing portion of a female cap that is compatible with the assembly of FIG. 1.
Figure 4B:
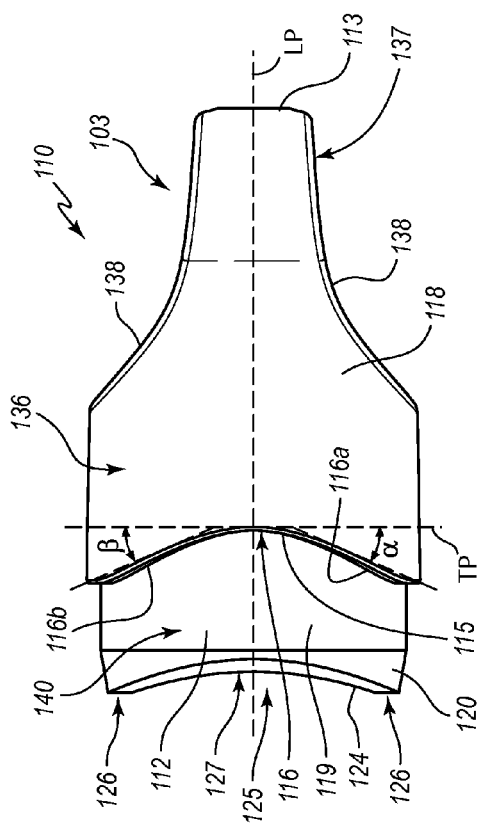
FIG. 4B is a side elevation view of the housing portion of the female cap of FIG. 4A.

As shown in FIG. 4B, the illustrated grasping platforms 138 are mirrored about a longitudinal plane LP that extends along a central longitudinal axis A (shown in FIG. 4A) of the housing 110. Each grasping platform 138 angles radially inwardly from the body region 136 toward the longitudinal plane LP, in a proximal-to-distal direction. The grasping platforms 138 are more steeply angled at their proximal ends than they are at their distal ends. The angled platforms 138, and particularly the steeply angled portions thereof, provide convenient surfaces to which forces may be applied in a distal-to-proximal direction. In the illustrated embodiment, the platforms 138 define two substantially planar regions that are smoothly joined to each other at a rounded transition. The platforms 138 can define a contour that is substantially complementary to fingertips that are pointed in the proximal direction.

As shown in FIG. 4A, the illustrated grasping platforms 138 also taper inwardly toward the central longitudinal axis A of the housing 110 in a proximal-to-distal direction. In the elevation view that is shown, the platforms 138 are substantially ovoid. The platforms 138 are sized and shaped to be held between the fingertips of a thumb and another finger (e.g., the index finger) of a user, although other grasping configurations may also be efficiently employed with the illustrated arrangement. The platforms 138 provide convenient surfaces to which torque may be applied so as to rotate the cap 102 about the longitudinal axis A.

With reference to FIGS. 4A-4C, the cap 102 can include a lip, rim, or flange 115 that extends radially inwardly at a proximal end of the body region 136. The flange 115 can contact the edge 198 of the sleeve 191 to ensure a desired insertion depth of the cap 102 within the sleeve 191. The flange 115 can define the one or more recesses 116 mentioned above.

With reference again to FIG. 4B, each recess 116 can be at least partially defined by a pair of faces 116a, 116b of the flange 115 that are angled in opposite directions. The angles can be any suitable non-zero, non-180-degree angles relative to a transverse cross-sectional plane TP that passes perpendicularly through the a central axis A of the housing 110. In particular, the faces 116a can define an angle α relative to the transverse plane TP, and the faces 116b can define an angle β relative to the transverse plane TP. In the illustrated embodiment, the angles α, β are the same, although other arrangements are possible (as discussed further below). For a path that is traced along the flange 115 in a clockwise direction (when looking toward the flange 115), the path moves proximally along the faces 116a and the path moves distally along the faces 116b. The faces 116a, 116b can be substantially planar over at least a portion thereof, and can be configured to complementarily contact the faces 199a, 199b, respectively, of the sleeve 191. Additional discussion of the faces 116a, 116b is provided below with respect to FIGS. 5A-5B.

The housing 110 defines an external surface 118 and an internal surface 119, each of which extends away from the flange 115. The internal surface 119 of the cap 102 can include an outwardly directed surface of the sidewall 112, a proximal end 124 of the sidewall 112, and an inwardly directed surface of the sidewall 112 (see FIGS. 4C and 6). The outwardly directed portion of the internal surface 119 can define a connection interface 140 that is configured to interact with or engage the connection interface 195 of the sleeve 191 so as to connect the cap 102 to the sleeve 191. In the illustrated embodiment, the connection interfaces 140, 195 couple with each other via a friction-fit engagement. For example, an inner diameter of the connection interface 195 of the sleeve 191 can be slightly smaller than an outer diameter of the connection interface 140 of the cap 102. The friction fit can be sufficiently strong to provide a fluid-tight seal between the cap 102 and the sleeve 191, yet can allow the cap 102 to be removed from the sleeve 191 via manipulation by a user (e.g., without the use of ancillary tools). The fluid-tight seal can prevent evaporative loss of antiseptic from an interior of the assembly 100 when it is in the pre-use configuration and/or can maintain the sterility of the internal portions of the assembly 100. In other or further embodiments, the connection interfaces 140, 195 can include threads and/or any other suitable attachment features. In the illustrated embodiment, a proximal portion of the connection interface 195 includes a chamfer 120, which can assist in centering the cap 102 relative to the sleeve 191 when connecting the cap 102 to the sleeve 191.

The proximal end 124 of the housing 110 (which is also a proximal end of the internal surface 119, or more generally, of the sidewall 112), can define a seal inhibitor 125, which can include one or more contact regions 126 and one or more venting regions 127. In the illustrated embodiment, the seal inhibitor 125 includes two contact regions 126 that are diametrically opposite from each other, and also includes two venting regions 127 that are diametrically opposite from each other and are angularly spaced from the contact regions. Other configurations of the seal inhibitor 125 are also possible, such as, for example, the seal inhibitors discussed in U.S. patent application Ser. No. 12/610,141, titled STERILIZATION CAPS AND SYSTEMS AND ASSOCIATED METHODS, filed Oct. 30, 2009, now published as U.S. Patent Application Publication No. 2010/0049170, which was previously incorporated by reference in this disclosure. For example, a portion of the seal inhibitor 125 can contact an outwardly projecting surface (e.g., a transverse planar surface) of a medical device with which that cap 102 is coupled. In particular, the proximal end 124 of the cap 102 can contact the surface at two separate contact regions 126 when the cap 102 is fully coupled with the connector. In contrast, the venting regions 127 can be spaced from the outwardly projecting surface of the connector. Such an arrangement can allow venting of antiseptic from a disinfecting chamber 122 defined by the housing 100, through the venting regions 127, and into the surrounding environment.

Figure 6:
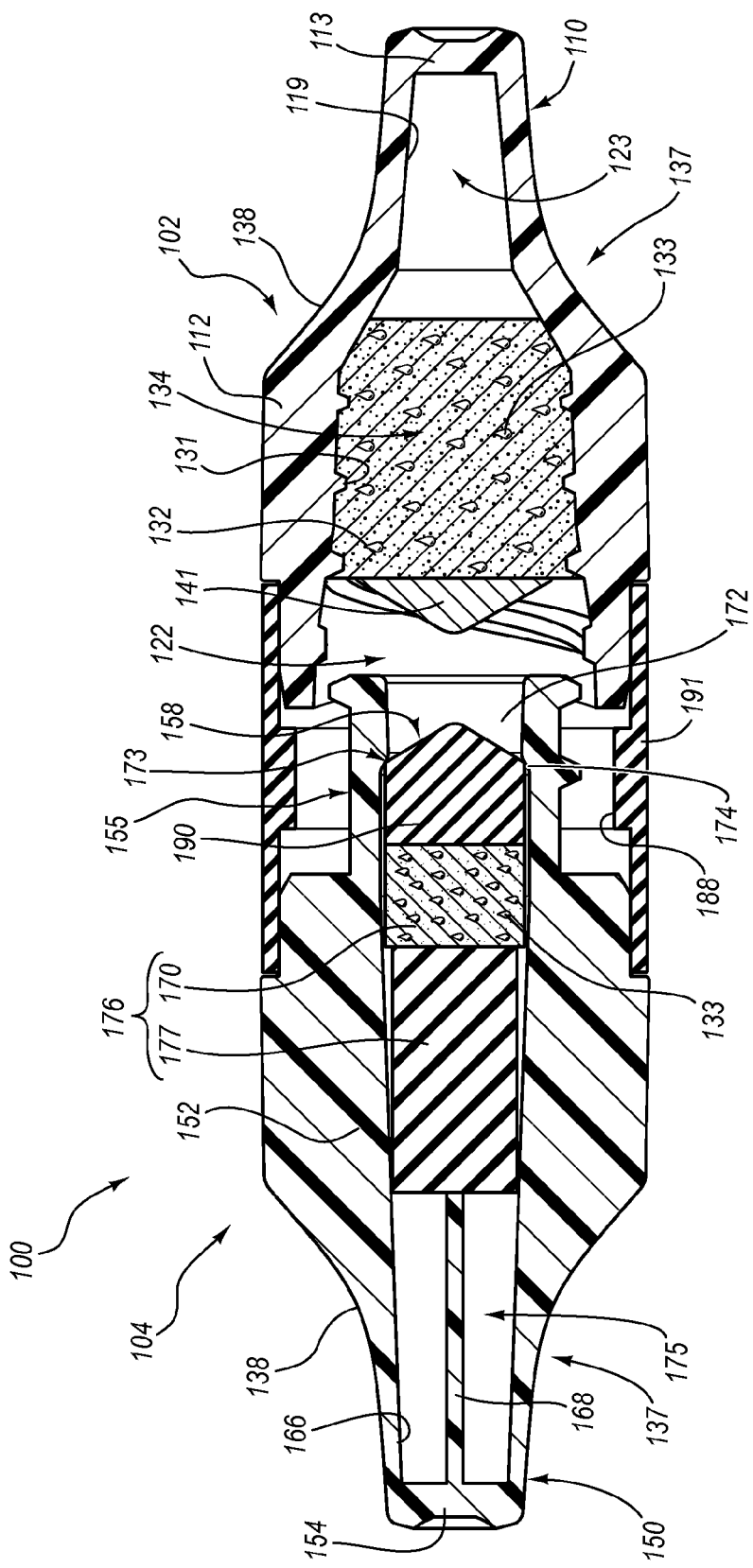
FIG. 6 is a cross-sectional view of the assembly of FIG. 1 taken along the view line 6-6 in FIG. 1.

With reference to FIGS. 4C and 6, the inwardly directed portion of the internal surface 119 of the sidewall 112 can define the disinfection chamber 122, which can include a connection interface 130. Any suitable connection system may be used for the connection interface 130. In the illustrated embodiment, the connection interface includes inwardly projecting threads 131. The connection interface 130 can be configured to attach the cap 102 to a medical connector in a secure yet selectively removable manner. For example, the cap 102 can be connected in any suitable manner with any suitable medical connector. In other embodiments, the connection interface 130 may include latches or prongs that are configured to snap over an outwardly extending rib of a connector, or may include one or more outwardly extending ribs over which one or more latches or prongs of the medical connector may snap.

A proximal portion of the disinfection chamber 122 can be larger than a distal extension 123 of the chamber. In the illustrated embodiment, the disinfection chamber 122 defines three substantially frustoconical regions. The proximal region has a slightly tapered outer boundary that decreases in cross-sectional area in the distal direction; the intermediate region has a more pronounced tapered outer boundary that more rapidly decreases in cross-sectional area in the distal direction; and the distal region or distal extension 123 has a slightly tapered outer boundary that decreases in cross-sectional area in the distal direction at about the same rate as the proximal region. The intermediate and distal regions correspond with the proximal and distal regions, respectively, of the grasping platforms 138.

The constricted intermediate region of the disinfection chamber 122 can provide a reactive force to a distal end of the pad 132 when the cap 102 is secured to a medical connector. The reactive force can be sufficient to prevent the pad 132 from being forced into the distal extension 123. In the illustrated embodiment, the threads 131 also provide resistive forces. Axial compression of the pad 132 as the cap 102 is coupled to a medical connector can swab the connector and deliver antiseptic 133 from the pad 132 into contact with the medical connector in manners such as described further below. In some embodiments, the pad 132 may be resiliently deformable so as to regain a pre-use shape after a medical connector is decoupled from the cap 102. In other embodiments, the pad 132 may instead be plastically deformable.

In various embodiments, the pad 132 can be configured to retain an antiseptic 133. For example, the pad 132 can comprise any suitable sponge-like material, such as an elastomeric foam, any open-cell foam, felt, or non-woven fiber matrix, and can be configured to conform to the contours of a portion of a medical connector that is introduced into the disinfection chamber 122 (e.g., uneven surfaces of an end of a female luer connector of any suitable variety; see also FIGS. 9-10C and the associated written description). The pad 132 can also comprise any closed-cell foam, as well as a solid elastomeric material such as silicone or the like.

The pad 132 can have a series or network of openings or spaces therein that can retain the antiseptic 133 when the pad 132 is in an expanded state. For example, the antiseptic 133 can be received within, occupy, fill (or partially fill), wet, soak, or saturate at least a fraction of the pad 132, or stated otherwise, can fill the pad 132 to a given concentration level. Compression of the pad 132 can cause antiseptic 133 to egress from the pad 132 so as to contact the medical connector. Resilient expansion of the foam upon removal of a compressive force can allow the pad 132 to soak up or absorb at least some of the antiseptic 133 that had previously been forced from the pad 132. In some embodiments, the antiseptic 133 can comprise any liquid antiseptic, such as, for example, alcohol (e.g., isopropyl alcohol) at various concentrations (e.g., ranging from 50-90%), ethanol at various concentrations (e.g., ranging from 50-95%), and combinations of any alcohols with any antiseptics, or a dry material, such as chlorhexidine, ethylenediaminetetraacetic acid (EDTA), lodaphors, or any suitable combination thereof. Accordingly, although the antiseptic 133 is schematically depicted in FIG. 6 as a series of droplets, the antiseptic 133 is not necessarily liquid and may fill the pad 132 to a greater or lesser extent than what is shown. In the illustrated embodiment, when the assembly 100 is in the pre-use condition, the pad 132 is in a relaxed, expanded, or uncompressed state in a longitudinal direction. It is noted that the pad 132 may be uncompressed in one or more dimensions, yet compressed in one or more other dimensions, when the assembly 100 is in the pre-use state. For example, the pad 132 can be expanded or in a relaxed state in a longitudinal direction, yet compressed radially inwardly via the sidewall 112, when the assembly 100 is in the pre-use state.

In the illustrated embodiment, the pad 132 is substantially square in cross-section along its full longitudinal length when the pad 132 is in a relaxed orientation (see FIG. 2). Such an arrangement can facilitate and/or reduce material costs associated with the manufacture of the pad 132. At least a portion of the pad 132 (e.g., the corners thereof) may be compressed radially when the pad 132 is positioned within the housing 112. Other rectangular cross-sections are also possible for the pad 132, and in other or further embodiments, the pad 132 may define a rectangular cross-section along only a portion of the longitudinal length thereof. In other embodiments, at least a portion of the pad 132 may define a round cross-section, such as a circular, elliptical, or other ovoid shape. For example, the pad 132 can be cylindrical so as to have a circular cross-section. The pad 132 may define any other suitable shape, and may or may not be radially compressed when the assembly 100 is in the pre-use state.

With reference to FIGS. 2 and 6, the sealing member 141 can be formed of any suitable material, such as, for example, an elastomer (e.g., silicone) or a thermoplastic, such as polypropylene, polycarbinate, acrylonitrile butadiene styrene (ABS), polyvinyl chloride (PVC), or rigid or semi-rigid thermoset plastic. The sealing member 141 can be formed in any suitable fashion, such as via molding or die cutting. In some embodiments, the sealing member 141 can be harder, more rigid, and/or less compliant than the pad 132. The sealing member 141 may be integral to the pad 132. For example, in some embodiments, the sealing member 141 may comprise a skin that is applied to the pad 132, or may comprise a modification of a surface of the pad 132 (e.g., melting, heat forming, or the like). In other embodiments, the sealing member 141 may be adhered to the pad 132 in any suitable fashion.

In the illustrated embodiment, the sealing member 141 is substantially conical. Such a shape can be well-suited for coupling with an end of a female luer connector, as further discussed below. Other shapes of the sealing member 141 are also possible, including, for example, flat or planar, disk-shaped, spherical, etc. As discussed with respect to other embodiments, at least a portion of the sealing member 141 may define a luer taper that complies with ISO luer standards (e.g., ISO 594-1:1986 and ISO 594-2:1998), such that the sealing member 141 can create a liquid-tight seal with a lumen of a female luer connector.

Figure 5C:
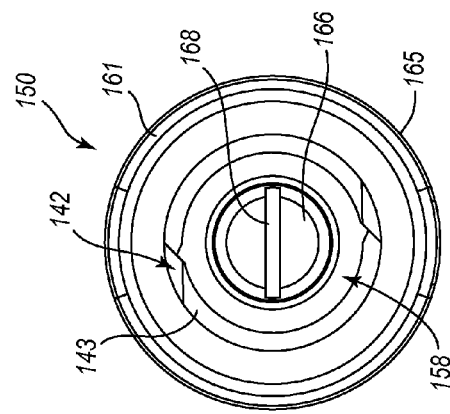
FIG. 5C is a front elevation view of the housing portion of the male cap of FIG. 5A.
Figure 5A:
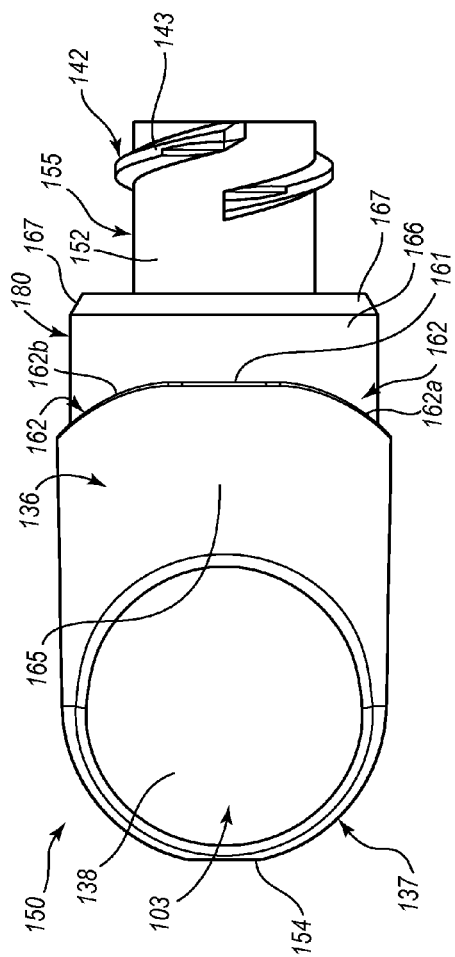
FIG. 5A is a top plan view of an embodiment of a housing portion of a male cap that is compatible with the assembly of FIG. 1.
Figure 5B:
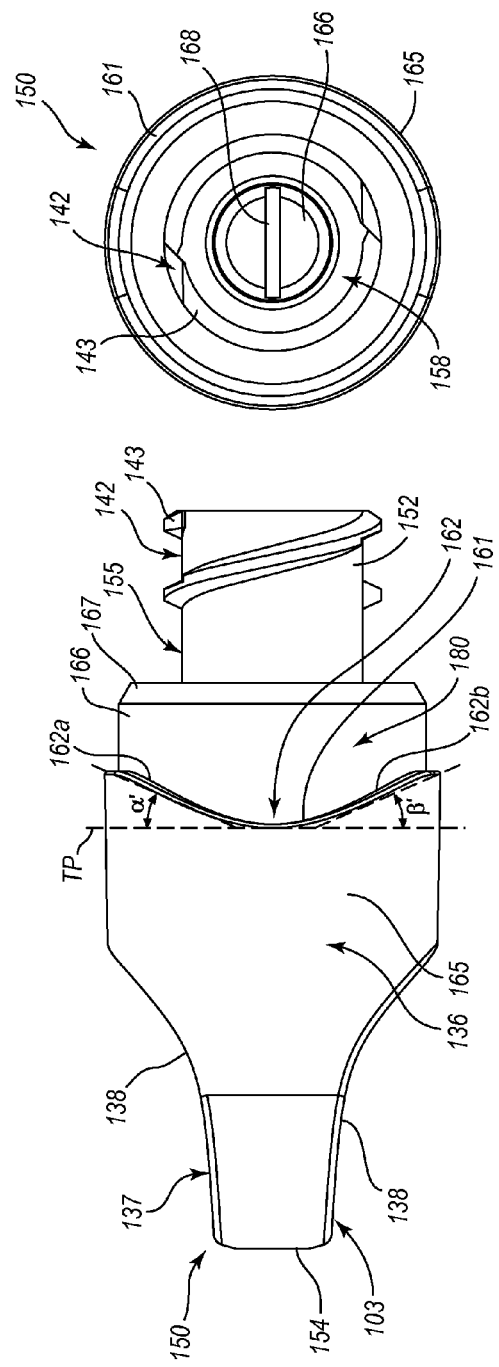
FIG. 5B is a side elevation view of the housing portion of the male cap of FIG. 5A.

With reference to FIGS. 5A-5C, the housing 150 of the male cap 104 can extend between a closed distal end and an open proximal end. The closed distal end does not permit any fluid flow therethrough and serves as a barrier between an interior of the housing 150 and an exterior environment. The open proximal end of the housing 150 is configured to receive at least a portion of a medical connector therein. In particular, the open proximal end of the housing 150 is sized and shaped to receive at least a portion of a male protrusion of a medical connector. For example, the open proximal end of the housing 150 can be configured to receive at least a portion of a male luer. The housing 150 can include a sidewall 152, which defines the open proximal end, and a base wall 154, which defines at least a portion of the closed distal end.

As viewed from the exterior (e.g., in FIGS. 5A and 5B), a shape and/or configuration of the distal end of the housing 150 can be similar or identical to the distal end of the housing 110 of the female cap 102, which is discussed above. For example, in the illustrated embodiment, the housing 150 includes a body region 136 and a handle 137 with grasping platforms 138, which when viewed exteriorly, are identical to the identically numbered features of the cap 102. Accordingly, as can be seen in FIGS. 1 and 6, when the assembly 100 is in the pre-use state, an exterior thereof can be symmetrical about three mutually perpendicular planes. Other arrangements are also possible.

With continued reference to FIGS. 5A-5C, the housing 150 can include a lip, rim, or flange 161 that extends radially inwardly at a proximal end of the body region 136. The flange 161 can contact the edge 196 of the sleeve 191 so as to ensure that the cap 104 is inserted into the sleeve 191 to the desired depth. The flange 161 can define the one or more recesses 162 mentioned above.

With reference to FIG. 5B, each recess 162 can be at least partially defined by a pair of faces 162a, 162b of the flange 161 that are angled in opposite directions. The angles can be any suitable non-zero, non-180-degree angles relative to a transverse cross-sectional plane TP that passes perpendicularly through the a central axis of the cap 104. In particular, the faces 162a can define an angle α' relative to the transverse plane TP, and the faces 162b can define an angle β' relative to the transverse plane TP. In the illustrated embodiment, the angles α', β' are the same, although other arrangements are possible (as discussed further below). Moreover, in the illustrated embodiment, the angles α', β' are identical to the angles α, β defined by the faces 116a, 116b of the cap 102. For a path is traced along the flange 161 in a clockwise direction (when looking toward the flange 161), the path moves proximally along the faces 116a and the path moves distally along the faces 116b. The faces 116a, 116b can be substantially planar over at least a portion thereof, and can be configured to complementarily contact the faces 197a, 197b, respectively, of the sleeve 191.

The male cap 104 defines an external surface 165 and an internal surface 166, each of which extends away from the flange 161. The internal surface 166 of the cap 104 can include an outwardly directed surface of the sidewall 152, a proximal end of the sidewall 152, and an inwardly directed surface of the sidewall 152 (see FIGS. 5C and 6). The outwardly directed portion of the internal surface 166 can define a connection interface 180 that is configured to interact with or engage the connection interface 193 of the sleeve 191 so as to connect the cap 104 to the sleeve 191. The connection interfaces 180, 193 can resemble the connection interfaces 140, 195 discussed above. In addition, a portion of the sidewall 152 that is at a proximal end of the connection interface 180 can include a chamfer 167, which can assist in centering the cap 104 relative to the sleeve 191 during connection of these components.

The sidewall 152 of the cap 104 can define an extension, elongated portion, or projection 155 that extends proximally from the connection interface 180. The projection 155 can be configured to couple with a medical connector that includes a male protrusion. The projection 155 includes a connection interface 142 that is configured to effect the coupling. In the illustrated embodiment, the projection 155 is substantially cylindrical, and the connection interface 142 comprises one or more threads 143 that are positioned at an outwardly facing surface of the cylinder. Any other suitable connection interface 142, such as any of those described above, is possible. In the illustrated embodiment, the reinforcement rib 188 of the sleeve 191 can be at a longitudinal center of the assembly 100, and the projection 155 can extend through the reinforcement rib 188.

With reference to FIGS. 5C and 6, an inwardly directed portion of the internal surface 166 of the sidewall 152 can define a disinfection chamber 158, which can extend from the proximal end of the projection 155 (i.e., the open proximal end of the cap 104) to the base wall 154. A proximal portion of the disinfection chamber 158 can include a proximal seal region 171, which can be configured to form a fluid-tight seal with the male protrusion portion of a medical connector. For example, the seal region 171 may be shaped complementarily to an outer surface of a male protrusion of a medical connector with which the male cap 104 is configured to be used. In the illustrated embodiment, the proximal seal region 171 comprises a substantially frustoconical surface 172 that complies with ISO luer standards (e.g., ISO 594-1:1986 and ISO 594-2:1998), such that a portion of a male luer can form a seal with the seal region 171. The frustoconical surface 172 can be tapered so as to decrease in diameter in a distal direction. In other embodiments, the proximal portion of the disinfection chamber 158 may not be configured to form a fluid-tight seal with a male protrusion of a medical connector.

The disinfection chamber 158 can further include an intermediate seal region 173. In the illustrated embodiment, the intermediate seal region is formed by a rim, ridge, lip, or shelf 174, which is defined by a short, substantially frustoconical portion of the sidewall 1052 that increases in diameter in the distal direction. An outer edge of a proximal surface of the sealing member 190 can define a greater outer diameter than a minimum inner diameter of the shelf 174 such that the shelf 174 can maintain the sealing member 190 within the chamber 158. The shelf 174 also can cooperate with the sealing member 190 to seal the chamber 158 when the assembly 100 is in the pre-use state, as further discussed below.

In the illustrated embodiment, a long distal extension 175 of the disinfection chamber 122 can extend distally from the shelf 174. The distal extension 123 has a slightly tapered outer boundary that gradually decreases in cross-sectional area in the distal direction. The disinfection chamber 122 can include a support column 168 within a distal region thereof. The support column 168 can be integrally formed with both the base wall 154 and the sidewall 152, and can provide a rigid surface against which the post 177 can rest. The support column 168 can act as a stop that prevents the post 177 from moving distally within the chamber 122 past a proximal end of the column 168. In some instances, however, a distal portion of the post 177 may deform so as to extend distally slightly past the proximal end of the support column 168 when a medical connector is coupled with the cap 104. The support column 168 can reduce the amount of material that might otherwise be used to form the handle 137 portion of the cap 104.

The post 177, which may also be referred to as a support or a base element, can be configured to provide a base against which the antiseptic reservoir or pad 170 can be compressed so as to force antiseptic 133 therefrom. Accordingly, the post 177 can be harder, stiffer, or less compliant than the pad 170, and can be configured to compress, under a given force, to a smaller extent than the pad 170 does under the same force. For example, in various embodiments, the post 177 can be no less than about 2, 3, or 4 times harder than the pad 170.

The post 177 can be elastically deformable such that compression of the post 177 from a relaxed orientation gives rise to a restorative force. The post 177 can naturally return to the relaxed orientation upon removal of the compressive force. The post 177 can comprise any suitable elastically deformable material. In some embodiments, the post 177 comprises an elastomeric material, such as silicone. In certain embodiments, the post 177 comprises a closed configuration (e.g., closed cell foam) or is otherwise nonabsorbent such that little or no antiseptic 133 that is expelled from the pad 170 is received into the post 177. In other or further embodiments, the post 177 may comprise a spring (e.g., a compression coil spring).

In the illustrated embodiment, a distal end of the post 177 seats snugly against the inner surface 166 of the sidewall 152. The post 177 may form a fluid-tight seal with the sidewall 152, which may prevent antiseptic 133 that is expelled from the pad 170 from migrating into the distal regions of the disinfecting chamber 158. Rather, the antiseptic 133 can be restrained to the proximal regions of the disinfecting chamber 158 where it can be urged into contact with a male protrusion of a medical connector.

The pad 170 can comprise any suitable material, such as those described above with respect to other pads (including plastically deformable materials, in some instances), and may be elastically or resiliently deformable. In some embodiments, the pad 170 is attached to the post 177 via any suitable adhesive or other attachment mechanism, although in other embodiments, no such attachment mechanisms are used. For example, the pad 170 and the post 177 may be maintained in contact with each other due to a slight longitudinal compression of one or more of these components once the cap 104 is assembled (e.g., once the post 177, the pad 170, and the sealing member 190 are positioned between the support column 168 and the shelf 174). Similarly, the pad 170 may be attached to the sealing member 190, or it may maintain a substantially fixed orientation relative to the sealing member 190 without such attachment due to the resilience of the pad 170 and/or the post 177, which are in a slightly compressed state.

In the illustrated embodiment, the pad 170 is substantially square in cross-section along its full longitudinal length when the pad 170 is in a relaxed orientation (see FIG. 2). Such an arrangement can facilitate and/or reduce material costs associated with the manufacture of the pad 170. At least a portion of the pad 170 (e.g., the corners thereof) may be compressed radially when the pad 170 is positioned within the housing 152. Other rectangular cross-sections are also possible for the pad 170, and in other or further embodiments, the pad 170 may define a rectangular cross-section along only a portion of the longitudinal length thereof. In other embodiments, at least a portion of the pad 170 may define a round cross-section, such as a circular, elliptical, or other ovoid shape. For example, the pad 170 can be cylindrical so as to have a circular cross-section. The pad 170 may define any other suitable shape, and may or may not be radially compressed when the assembly 100 is in the pre-use state.

As previously mentioned, the pad 170 and the post 177 can, in some embodiments, cooperate as a two-part support member 176. It is to be understood that any other suitable support members 176 may be used. In some embodiments, one or more of the pad 170 and post 177 may be plastically deformable, such that the support member 176 is merely compressible. In other embodiments, such as that illustrated in the present drawings, the pad 170 and the post 177 can be resiliently deformable such that a restorative force arises when the support member 176 is compressed. The support member 176 thus may also be referred to as a biasing member 176, in certain instances.

In the illustrated embodiment, the biasing member 176 can urge the sealing member 190 in the proximal direction into sealing contact with the shelf 174. The seal thus formed may be fluid-tight, and may prevent antiseptic 133, whether in liquid or vapor form, from exiting the disinfecting chamber 158 through the proximal end of the cap 104 prior to coupling of the cap 104 to a medical connector. This proximal seal may be in place when the assembly 100 is in the pre-use configuration, as well as after the separation of the male and female caps 104, 102 when the assembly 100 is opened.

The illustrated sealing member 190 comprises unitary piece of material that includes a cylindrical region and a conical region. The conical region can be well-suited to form a seal with a tip of the projection of a male medical connector in manners such as described above. In some instances, an apex of the conical region can be received within a lumen of a luer when a medical connector is coupled with the cap 104

Figure 8A:
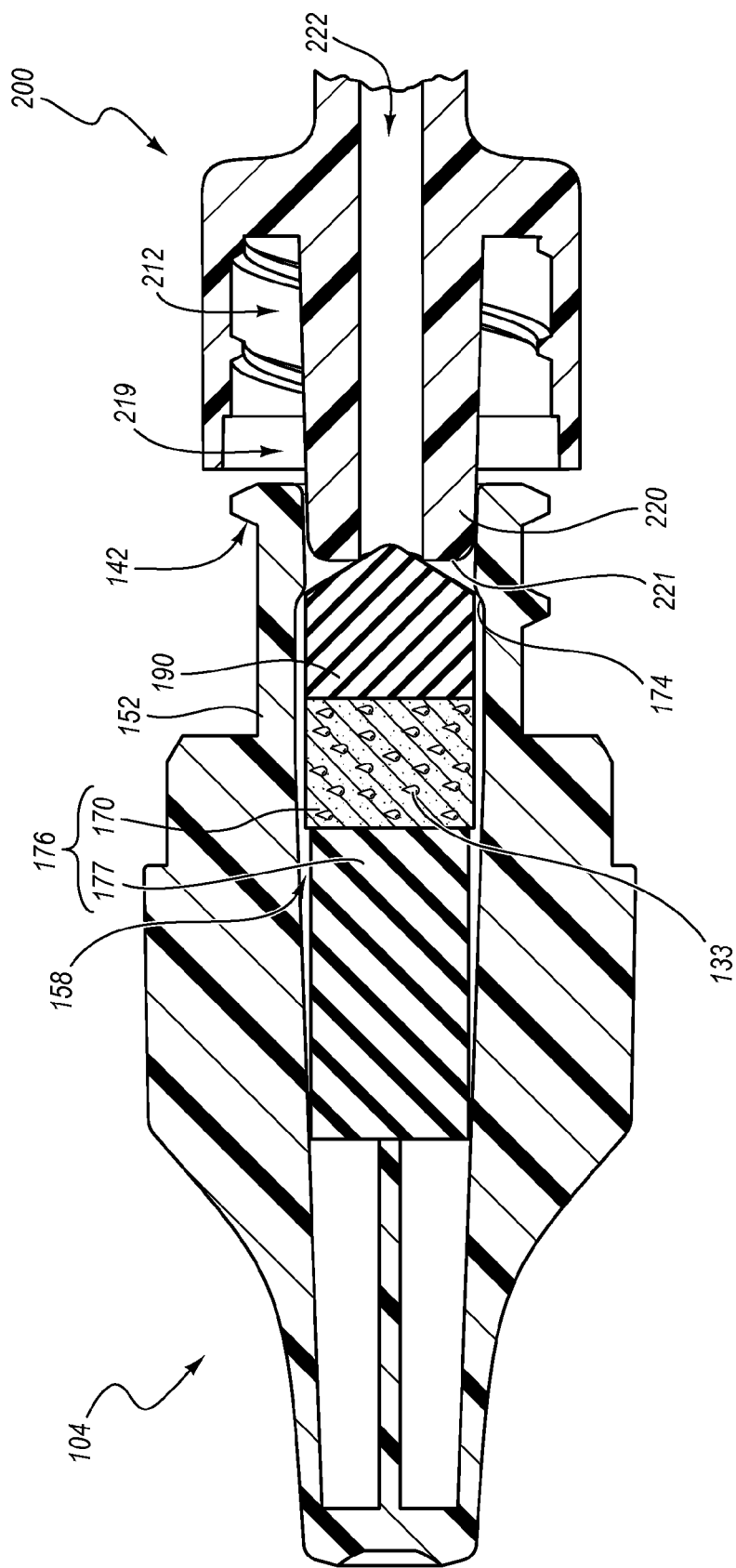
FIGS. 8A-8D are cross-sectional views that depict various stages of an illustrative method for coupling a medical connector with the male cap of FIGS. 1 and 6.

(see, e.g., FIG. 8A). The sealing member 190 can be formed of any suitable material, such as, for example, an elastomer (e.g., silicone) or a thermoplastic, such as polypropylene, polycarbinate, acrylonitrile butadiene styrene (ABS), polyvinyl chloride (PVC), or rigid or semi-rigid thermoset plastic. The sealing member 190 can be formed in any suitable fashion, such as via molding or die cutting. In some embodiments, the sealing member 190 can be harder, more rigid, and/or less compliant than the pad 170. The sealing member 190 may be integral to the pad 170. For example, in some embodiments, the sealing member 190 may comprise a skin that is applied to the pad 170, or may comprise a modification of a surface of the pad 170 (e.g., melting, heat forming, or the like). Other shapes of the sealing member 190 are possible, including, for example, flat or planar, disk-shaped, spherical, etc.

FIGS. 7A and 7B illustrate stages in a method of removing the male cap 104 from the assembly 100. In some embodiments, it can be particularly advantageous to use the separation assists 108 in the removal process. For example, in some instances, the fluid-tight seal between the cap 104 and the sleeve 191 can be relatively tight and/or a slight vacuum may be present within the assembly 100 (and/or may arise as the cap 104 is removed from the assembly 100), such that the separation assists 108 can facilitate removal of the cap 104.

FIG. 7A illustrates the assembly 100 in the pre-use state, with the faces 162a, 197a and 162b, 197b of the surfaces 161, 196 in contact with each other. Each paired set of surfaces constitutes a separation assist 108. In the illustrated embodiment the assembly 100 includes four separation assists 108 rotationally spaced from each other at intervals of approximately 90 degrees. Focusing now on the upper separation assist 108 that includes the faces 162b, 197b, the face 162b can define an angle β' (see FIG. 5B) of about 20 degrees. The face 197b of the sleeve 191 is at the same angle, although oppositely directed.

In order to separate the cap 104 from the sleeve 191, the cap 104 can be rotated relative the sleeve 191. In the illustrated embodiment, the cap 104 is rotated counterclockwise, which can cause the faces 162b, 197b to interact with each other and slide past each other. The cap 104 thus cams relative to the sleeve 191 as the rotational motion is converted into translational movement of the cap 104 away from the sleeve 191, as shown by the arrow in FIG. 7B.

Where the angles α', β' (see FIG. 5B) of the surfaces 162a, 162b are identical, the same mechanical advantage may be present whether the cap 104 is rotated in the clockwise or counterclockwise directions. In other embodiments, the separation assists 108 can be configured to aid in separating the cap 104 from the sleeve 191 only when the cap 104 is rotated in one predetermined direction (e.g., either clockwise or counterclockwise). For example, the pair of faces 162a or the pair of faces 162b may define an angle α' or β', respectively, of 20 degrees so as to allow separation as shown in FIG. 5B, whereas the other pair of faces 162a, 162b may be at an angle of about 90 degrees (i.e., approximately parallel to or extending through a central axis of the cap 104) so as to prevent rotation and separation of the cap 104. In other embodiments, one or more of the faces 162a, 162b may be at larger or smaller angles α', β'. For example, one or more of the angles α', β' may be no more than about 15, 20, 1, 45, 60, or 75 degrees or no less than about 15, 20, 1, 45, 60, or 75 degrees. Other configurations of the separation assists 108 are also possible. For example, in some embodiments, the complementary surfaces of the recess 162 and the protrusion 199 can define angles as just described, but the surfaces may be rounded or otherwise non-planar.

The foregoing discussion regarding the separation assists 108 applies equally to the separation assists 107. In the illustrated embodiment, the separation assists 107, 108 are substantially identical. The sleeve 191 may be reversible, as either end thereof may connect with either cap 102, 104. In other embodiments, the arrangements of the separation assists 107, 108 may be different from each other. For example, the planar surfaces of the separation assist 107 may be at a larger or smaller angle than those of the separation assist 108 so as to provide a different amount of separation force. Moreover, in some embodiments, the assembly 100 includes a number of separation assists 107 equal to the number of separation assists 108, whereas in other embodiments, the assembly 100 may include more or fewer separation assists 107 as compared with the number of separation assists 108. Other arrangements of the separation assists 107, 108 are contemplated, including those discussed above with respect to the assembly 2700. Other embodiments may be devoid of the separation assists 107, 108. Moreover, in some instances, a user may remove one or more of the caps 102, 104 from the assembly 100 in a substantially longitudinal direction only (e.g., without rotating the caps 102, 104 relative to each other).

FIGS. 8A-8D illustrate consecutive stages of the cap 104 being coupled with a medical device 200 that includes a male protrusion 219, which in the illustrated embodiment is a male luer 220. As mentioned above, other arrangements of the male protrusion 219 are also contemplated. A tip 221 of the protrusion 219, can be received within the disinfection chamber 158 prior to contacting the sealing member 190. Stated otherwise, the sealing member 190 can be recessed relative to a proximal end of the sidewall 152 by a distance that is sufficiently great to permit at least a portion of the male luer 220 to be received within the sidewall 152 before the male luer contacts the sealing member 190.

In the illustrated stage of the procedure, the luer 220 has been advanced sufficiently far into the disinfection chamber 158 to contact the sealing member 190 and to form a seal therewith. The connection interface 142 of the cap 104 has not yet engaged a connection interface 212 of the medical connector 200 at this stage, and the sealing member 190 is just beginning to move from its initial orientation, or position, in a distal direction within the disinfection chamber 158 so as to break the proximal seal between the sealing member 190 and the shelf 174. The support member 176, which is also in an initial orientation, can resist such distal movement of the sealing member 190, which resistive force can be sufficient to create the seal between the sealing member 190 and the luer 220 and thereby seal the fluid path 222.

Figure 8B:
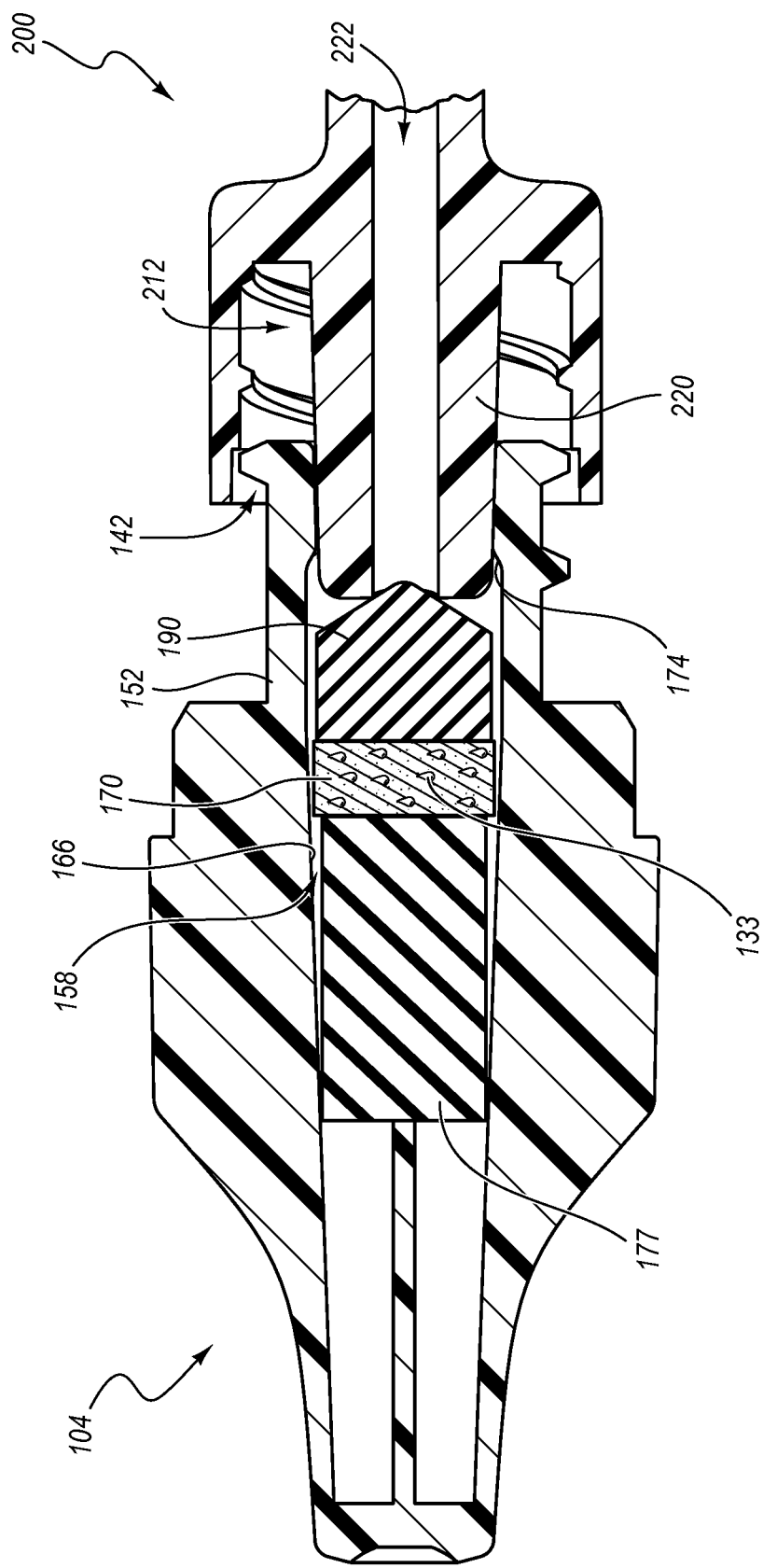

In FIG. 8B, the luer 220 has been advanced slightly further into the disinfection chamber 158, thereby compressing the pad 170 somewhat and forcing antiseptic 133 out of the pad 170. The sealing member 190 can define an outer diameter that is smaller than an inner diameter of this portion of the disinfection chamber 158 such that a fluid path is present about an exterior of the sealing member 190. Stated otherwise, the sealing member 190 has been urged distally to a position where a periphery or outermost perimeter of the sealing member 190 is spaced from the sidewall 152 such that an opening, spacing, or gap that exists between the sealing member 190 and the sidewall 152. This opening may function as a fluid port.

Antiseptic 133 thus can flow about the sealing member 190 and/or any other portion of an open region that exists between the inner surface 166 of the sidewall 152 and the outer surfaces of the post 177, the pad 170, the sealing member 190, and the luer 220. Further advancement of the luer 220 into the disinfection chamber 158 can cause the antiseptic 133 to fill this open region. However, the antiseptic 133 does not enter into a fluid path, fluid passageway, or lumen 222 of the luer 220 due to the seal between the luer 220 and the sealing member 190. Further advancement of the luer 220 into the disinfection chamber 158 also can strengthen the seal between the luer 220 and the sealing member 190 due to the increasing restorative forces that arise as the pad 170 is compressed.

As the pad 170 is softer or more compliant than the post 177, the pad 170 has been compressed to a much greater extent than the post 177 at this stage. Indeed, in some embodiments, the post 177 may compress only slightly or not at all at this stage.

In the illustrated embodiment, the interfaces 142, 212 have not yet coupled with each other at this stage. However, in other embodiments, the interfaces 142, 210 may already cooperate with each other at this or at a previous stage so as to draw the luer 220 into the disinfection chamber 158.

Figure 8C:
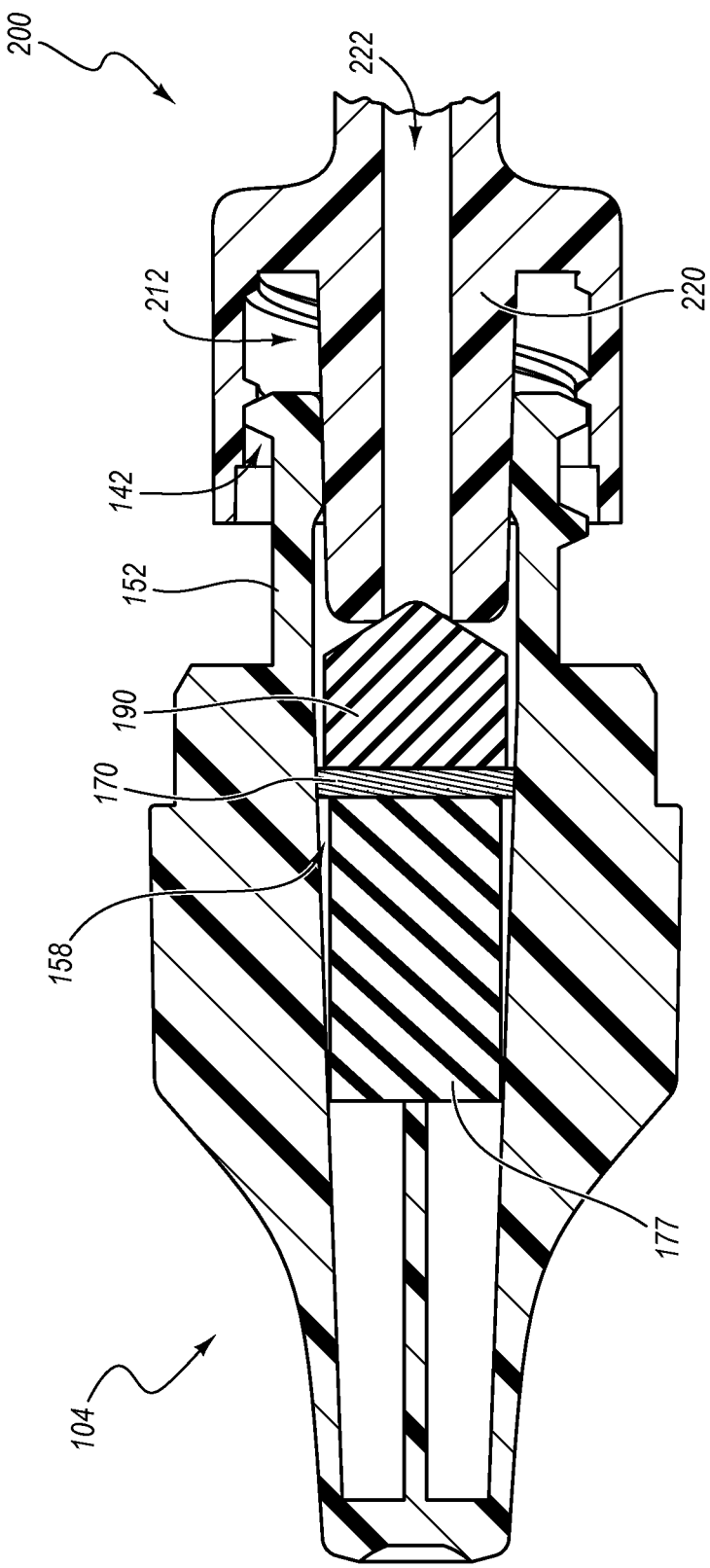

In FIG. 8C, the luer 220 has been advanced even further into the disinfection chamber 158, thereby compressing the pad 170 to a greater extent and forcing additional antiseptic 133 into the interior regions of the disinfection chamber 158. In the illustrated embodiment, the post 177 is shown as having been slightly compressed relative to its configuration in the stage shown in FIG. 8C, whereas the pad 170 has been nearly completely compressed, such that all or nearly all of the antiseptic 133 has been forced therefrom. Cooperation between the connection interfaces 142, 212 can facilitate compression of the pad 170 and/or the post 177.

Although the outer surface of the luer 220 appears to be nearly parallel to and in contact with the luer-tapered surface 172 of the sidewall 152, a fluid-tight seal may not have formed yet in this area. Accordingly, the antiseptic 133 may be permitted to cover the portion of the luer 220 that is within the chamber 158, while in some embodiments, a small portion of antiseptic 133 may also be permitted to exit from the disinfection chamber 158. The portion of the luer 220 that is within the disinfection chamber 158 thus may contact the antiseptic 133 so as to be disinfected thereby.

Figure 8D:
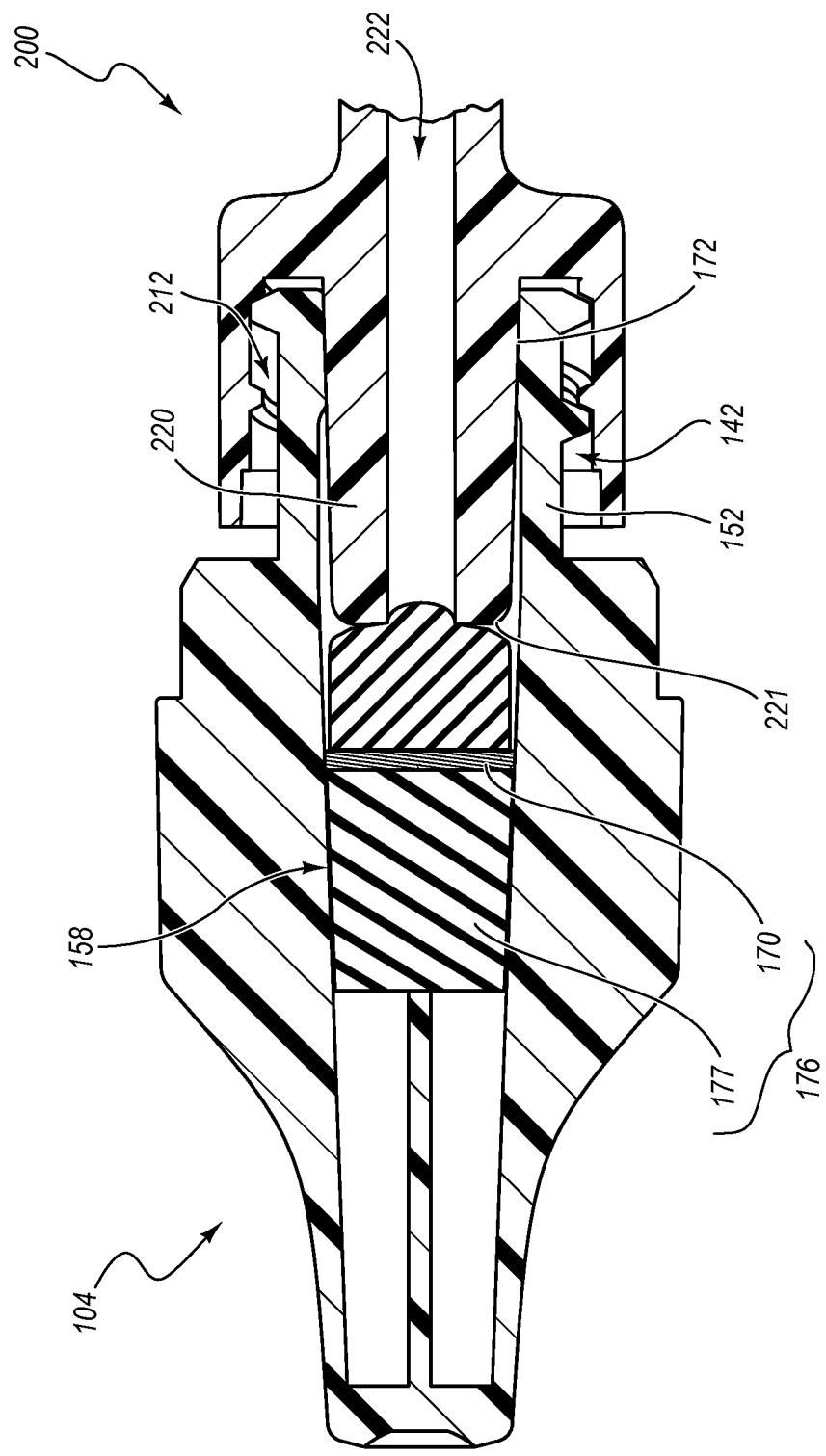

FIG. 8D illustrates a final or fully coupled stage or an end-of-stroke orientation, in which the sealing member 190 has been moved distally within the chamber 158 to a retracted orientation. The retracted orientation thus can correspond with a final position of the sealing member 190 when the medical connector 200 has been fully coupled with the cap 104. When it is in the retracted orientation, the sealing member 190 is spaced from the proximal end of the sidewall 152 by a greater distance than it was when in the initial orientation shown in FIG. 8A. Stated otherwise, the sealing member 190 can been moved from the initial orientation (FIG. 8A) to the retracted orientation (FIG. 8D) so as to space the sealing member 190 from the connection interface 142 by a progressively greater amount. Similarly, or correspondingly, the support member 176 can been moved from the initial orientation (FIG. 8A) to the retracted orientation (FIG. 8D) so as to space a proximal end of the support member 176 from the connection interface 142 by a progressively greater amount. In some instances, the initial and retracted orientations may be described relative to the connection interface 142, since the connection interface 212 of the medical connector 200 and the connection interface 142 of the cap 104 can cooperate with each other to advance the luer 220 deeper into the chamber 158, and as a result, advance the sealing member 190 and the support member 176 to deeper positions within the disinfecting chamber 158.

In the illustrated embodiment, when the sealing member 190 has reached this retracted orientation, the luer 220 has been advanced even further into the disinfection chamber 158 such that the luer 220 forms a seal with the luer-tapered surface 172 of the sidewall 152. Antiseptic 133 can be retained in all open portions of the disinfection chamber 158 that are between the seal formed by the luer 220 and the sealing member 190 and the seal formed by the luer 220 and the sidewall 152. In the illustrated embodiment, a relatively large portion of the luer 220, which includes all or most of the tip 221, is in continual contact with the portion of the antiseptic 133 thus retained. This portion of the luer 220 can be bathed by the antiseptic 133 and disinfected thereby. In other embodiments, larger portions of the luer 220 can be bathed.

The deformable nature of the post 177 can allow for distal movement of the pad 170, even after the pad 170 has been fully compressed. Such an arrangement can allow for a range of acceptable lengths and diameters for the luer 220. For example, shorter luers 220 than that illustrated in the drawings may still be able to fully compress the pad 170 so as to expel all antiseptic therefrom.

In other embodiments, the medical connector 200 may include a male protrusion other than a luer 220, such as a male protrusion that is shaped substantially as a cylinder or in some other configuration, such as a taper having dimensions other than those of a standard luer. In some embodiments, the surface 172 may be shaped complementarily to the outer surface of such protrusions so as to for a seal therewith. In still other embodiments, the sidewall 152 may not form a seal with the protrusion.

When the luer 220 is removed from the chamber 158, the restoration forces of the pad 170 and/or the post 177 (i.e., the resilient biasing member 176) can maintain the seal between the luer 220 and the sealing member 190, which can prevent antiseptic from entering into the lumen 222 of the luer 220. The sealing member 190 can be returned to the initial orientation shown in FIG. 8A.

Figure 9:
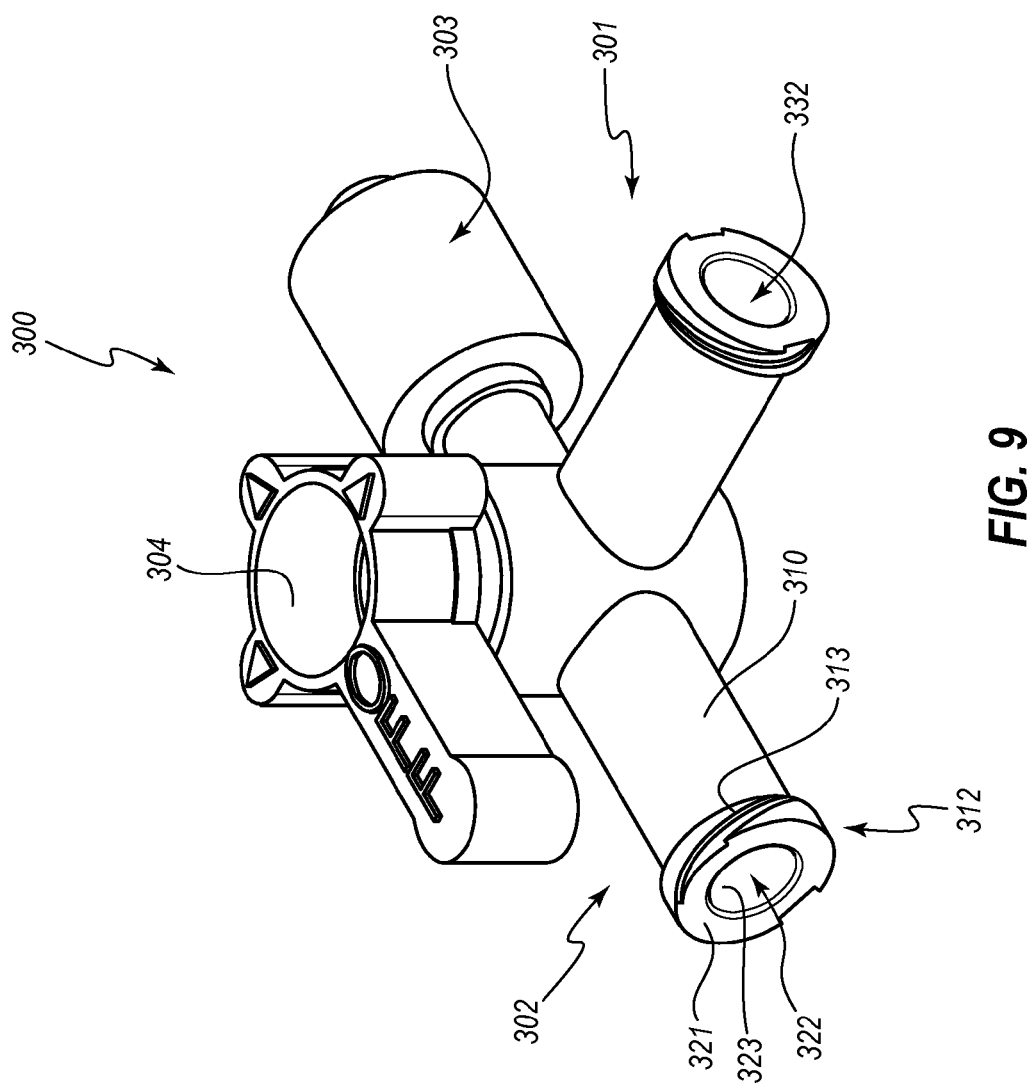
FIG. 9 is a perspective view of an embodiment of a medical connector with which various embodiments of caps can be used.

FIG. 9 illustrates an embodiment of a medical connector assembly 300 with which the female cap 102 can be coupled. Any suitable medical connector or medical connector assembly is contemplated, particularly those that define one or more open female lumens. The illustrated medical connector assembly 300 comprises a medical stopcock valve assembly that includes a plurality of fluid-directing tubes, each having a connection interface. The connector assembly 300 can be formed of any suitable material, such as, for example, plastic. In the illustrated embodiment, the assembly 300 comprises a first port or female connector portion 301 and a second port or female connector portion 302 that can be placed in selective communication with a third port or male connector portion 303 via a valve or direction control member 304. The direction control member 304 is rotatably arranged within the valve body for selectively closing one or more ports while opening communication between at least two other ports. The medical connector assembly 300 may be used in any of a variety of medical procedures and operations, such as, for example, metering the infusion of fluids into patients. A female cap 102 can be used with one or more of the female connector portions 301, 302, such as when the respective female connector portion or port is not in use.

In the illustrated embodiment, the female connector portions 301, 302 each comprise a female luer lock fitting, although other arrangements are also possible. With reference in particular to the port or connector 302, the connector 302 can include a sidewall 310 that includes a connection interface 312 at a proximal end thereof. The Connection interface 312 can include any suitable arrangement, and can be configured to cooperate with the connection interface 130 of a female cap 102 so as to couple the cap to the connector 302 in a secure yet selectively removable manner. In the illustrated embodiment, the connection interface 312 comprises threading 313. The sidewall 310 can define a proximal end or proximal face 321 and an interior surface 323. The interior surface 323 can define an open female lumen 322, which can define a fluid path or passageway through which fluids can flow through the assembly 300.

Figure 10A:
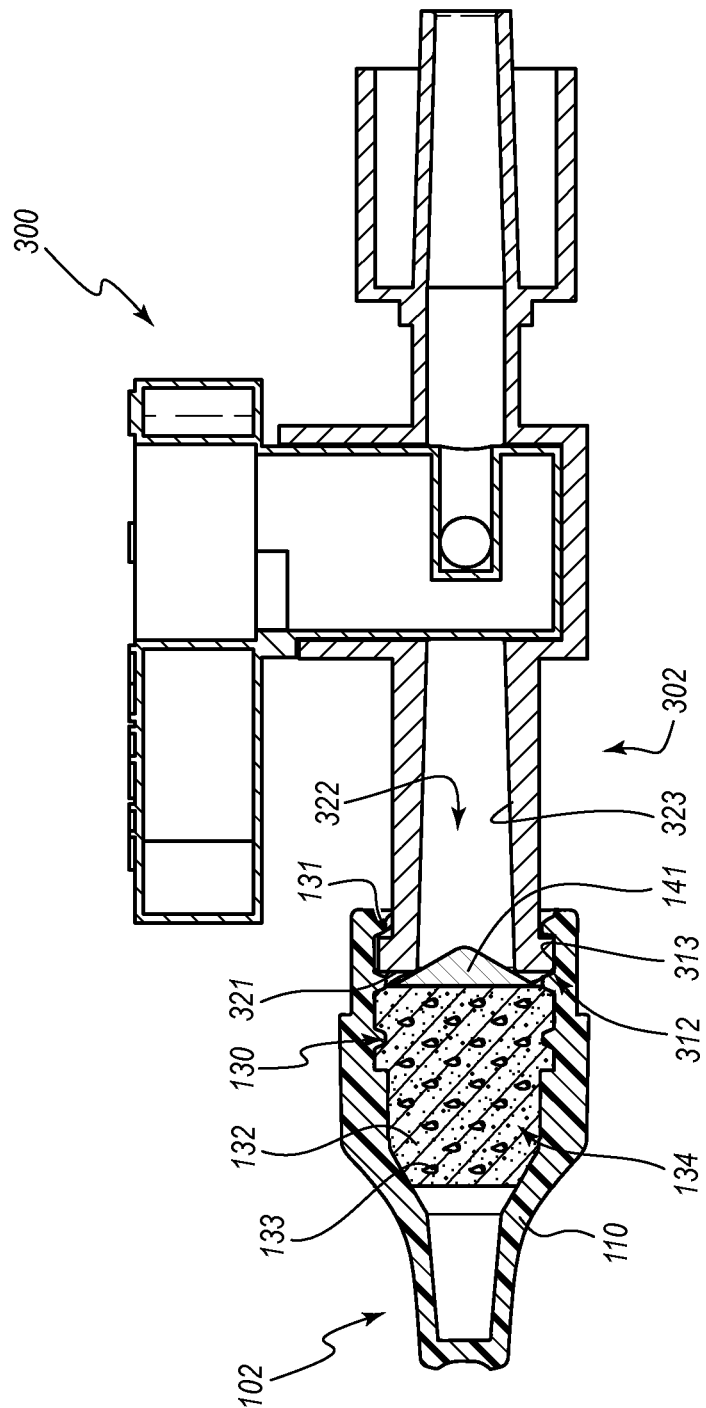
FIGS. 10A-10C are cross-sectional views that depict various stages of an illustrative method for coupling the medical connector of FIG. 9 with the female cap of FIGS. 1 and 6.
Figure 10B:
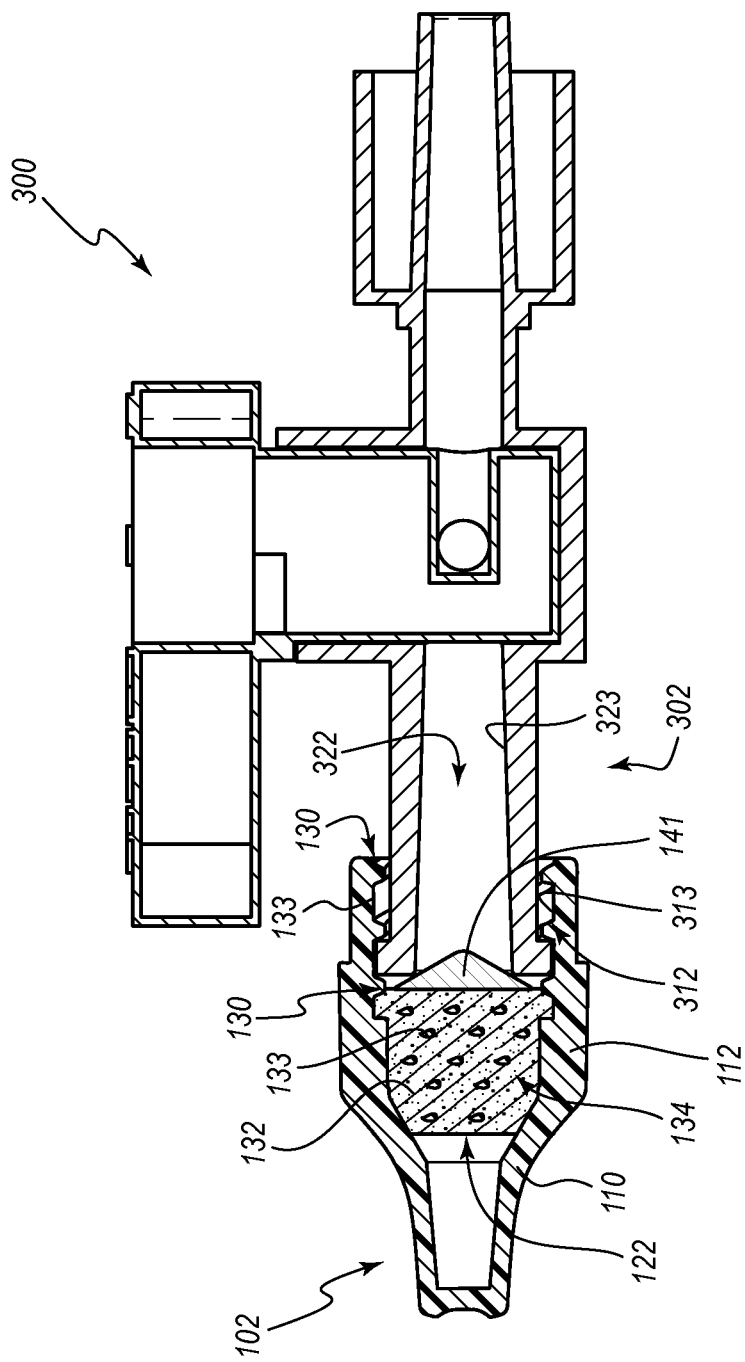
Figure 10C:
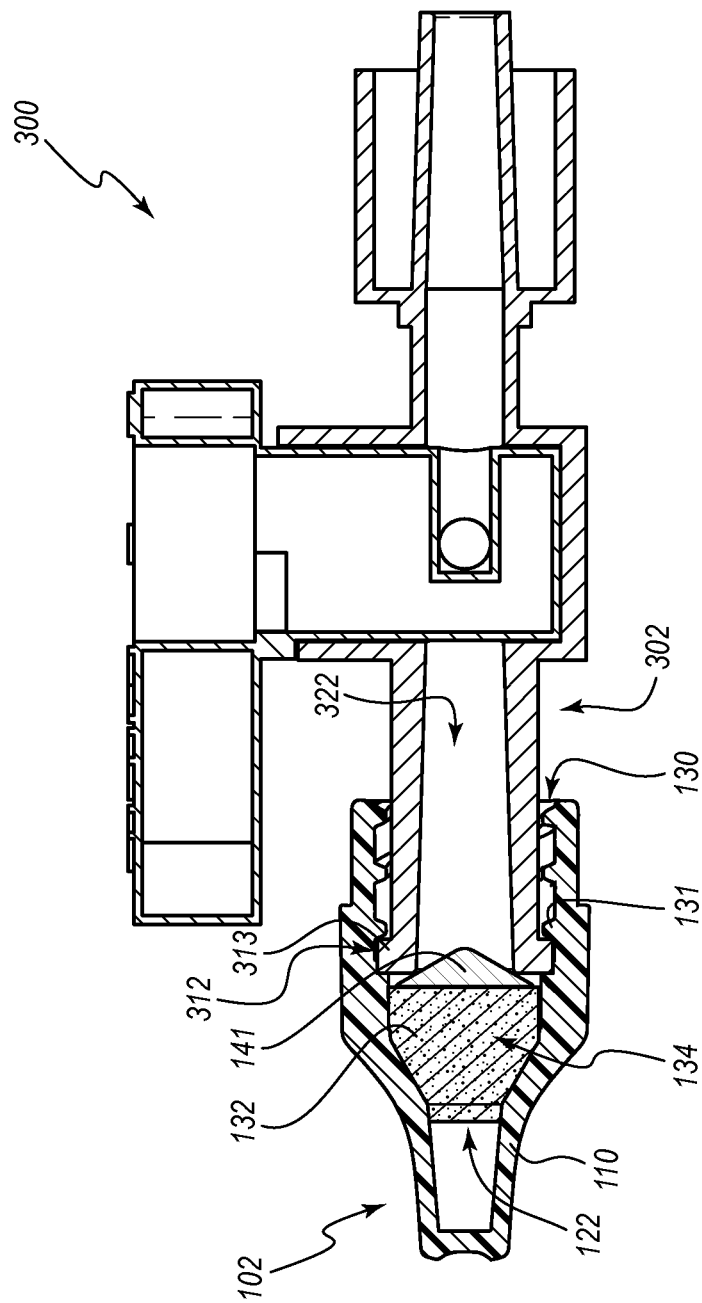
Figure 11:
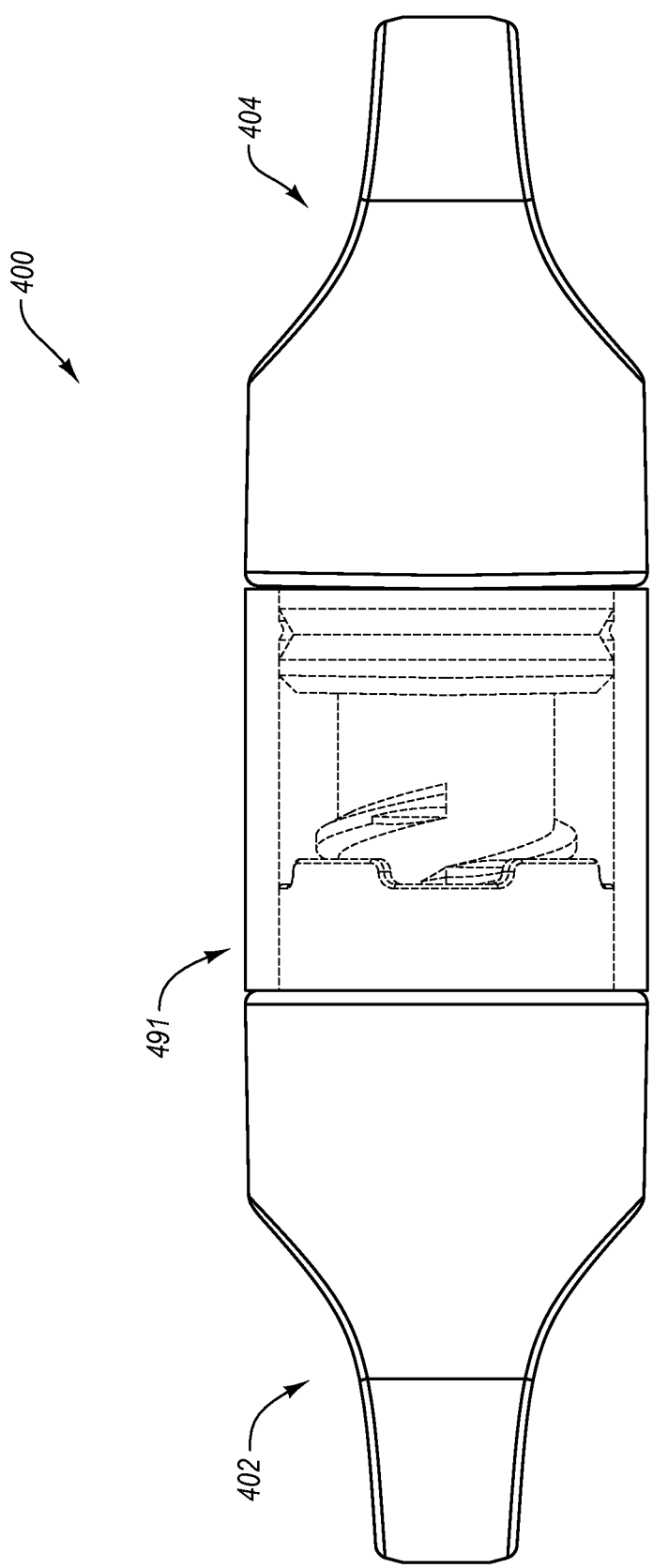
FIG. 11 is a side elevation view of another embodiment of an assembly that includes an embodiment of a female cap and an embodiment of a male cap, which can be connected in a pre-use configuration via a sleeve.

FIGS. 10A-10C illustrate consecutive stages of the cap 102 being coupled with the port 302 of the connector assembly 300. The coupling may proceed in a manner similar to coupling the cap 104 with a male medical connector 200, as discussed above with respect to FIGS. 8A-8D.

With reference to FIG. 10A, the connection interface 130 of the housing 110 can be coupled with the connection interface 312 of the port 302. In some embodiments, this coupling can take place before contact between a proximal end of the port 302 and the sealing member 141 occurs. The cap 102 can be rotated relative to the port 302 so as to further engage the threads 131, 313 and advance the cap 102 over the port 302. Upon sufficient advancement of the cap 102 over the port 302, the sealing member 141 can contact the proximal face 321 and/or the interior surface 323 of the port 302. In the illustrated embodiment, the sealing member 141 initially contacts a ring of the port 302 at which the proximal face 321 and the interior surface 323 meet.

In the illustrated stage of the procedure, the port 302 has been advanced sufficiently far into the disinfection chamber 122 to contact the sealing member 141 and to form a seal therewith. The sealing member 141 is just beginning to move from its initial orientation, or position, in a distal direction within the disinfection chamber 122. The pad 132, acting as the support member 134, opposes the distal movement of the sealing member 141, thereby providing sufficient resistive force for the creation of the seal. As shown in FIG. 10A, the support member 134 is also in an initial orientation. Substantially no antiseptic 133 has been expelled from the pad 132 at this stage.

In FIG. 10B, the port 302 has been advanced slightly further into the disinfection chamber 122, thereby compressing the pad 132 somewhat and forcing antiseptic 133 out of the pad 132. The sealing member 141 can define an outer diameter that is smaller than an inner diameter of this portion of the disinfection chamber 122 such that a fluid path is present about an exterior of the sealing member 132. Stated otherwise, the sealing member 141 has been urged distally to a position where a periphery or outermost perimeter of the sealing member 141 is spaced from the sidewall 112 such that an opening, spacing, or gap that exists between the sealing member 141 and the sidewall 112. This opening may function as a fluid port.

Antiseptic 133 thus can flow about the sealing member 141 and into contact with the port 302. However, the antiseptic 133 does not enter into the fluid path 322 of the port 302 due to the seal between the port 302 and the sealing member 141. Further advancement of the port 302 into the disinfection chamber 122 also can strengthen the seal between the port 302 and the sealing member 141 due to the increasing restorative forces that arise as the pad 132 is compressed.

In the illustrated embodiment, only a relatively small contact area is maintained between the sealing member 141 and the port 302, but this area can be sufficient to form and maintain a fluid-tight seal that prevents antiseptic 133 from entering the fluid path 322. In other embodiments, the sealing member 141 can be configured to plug the fluid path 322 and/or contact a larger portion of the inner surface 323, as discussed further below with respect to FIGS. 12-15.

FIG. 10C illustrates a final or fully coupled stage or an end-of-stroke orientation, in which the sealing member 141 has been moved distally within the chamber 122 to a retracted orientation. The retracted orientation thus can correspond with a final position of the sealing member 141 when the cap 102 has been fully coupled with the port 302. When it is in the retracted orientation, the sealing member 141 is spaced from the proximal end of the housing 110 by a greater distance than it was when in the initial orientation shown in FIG. 10A. Stated otherwise, the sealing member 141 can been moved from the initial orientation (FIG. 10A) to the retracted orientation (FIG. 10C) so as to space the sealing member 141 from the connection interface 130 by a progressively greater amount. Similarly, or correspondingly, the support member 134 can be moved to a retracted orientation in which it has been compressed such that a proximal end thereof is further from the connection interface 130 than it was when the support member 134 was in its initial orientation. In some instances, the initial and retracted orientations may be described relative to the connection interface 130, since the connection interface 130 of the cap 102 and the connection interface 312 of the port 302 can cooperate with each other to advance the port 302 deeper into the chamber 122, and as a result, advance the sealing member 141 and the proximal end for the support member 134 to deeper positions within the chamber 122.

In the illustrated embodiment, when the sealing member 141 has reached this retracted orientation, the port 302 has been advanced even further into the disinfection chamber 122. Antiseptic 133 can be permitted to flow to all open portions of the disinfection chamber 122, and thus may bathe, disinfect, or clean an exterior surface of the port 302.

When the port 302 is removed from the chamber 122, the restoration forces of the pad 132 can maintain the seal between the port 302 and the sealing member 141, which can prevent antiseptic from entering into the lumen 322. The sealing member 141 can be returned to the initial orientation shown in FIG. 10A.

FIGS. 11-15 illustrate another embodiment of an assembly 400 that includes an embodiment of a female cap 402 and an embodiment of a male cap 404, which can resemble the assembly 100 and caps 102, 104 described above in certain respects. Accordingly, like features are designated with like reference numerals, with the leading digits "1" incremented to "4." Relevant disclosure set forth above regarding similarly identified features thus may not be repeated hereafter. Moreover, specific features of the assembly 400 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the assembly 400. Any suitable combination of the features and variations of the same described with respect to the assembly 100 can be employed with the assembly 400, and vice versa. Such disclosure methods apply to additional embodiments disclosed hereafter, such as those shown in each of FIGS. 16-19B, 20, 21, 22, 23A-23C, and 24.

The caps 402, 404 can be coupled to each other via a sleeve 491. In the illustrated embodiment, the assembly 400 is devoid of separation assists, such as those described above with respect to the assembly 100.

Figure 12:
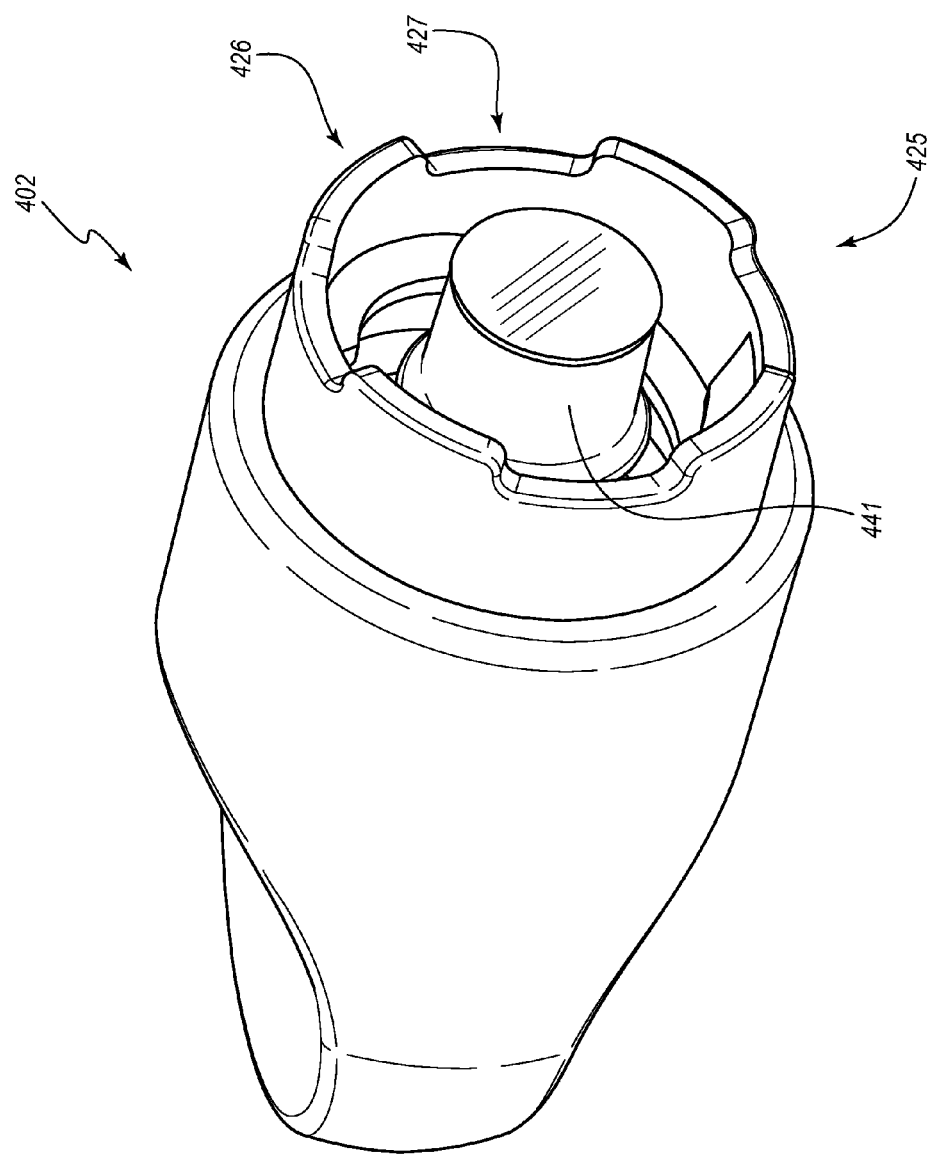
FIG. 12 is a perspective view of the female cap of FIG. 11.
Figure 13:
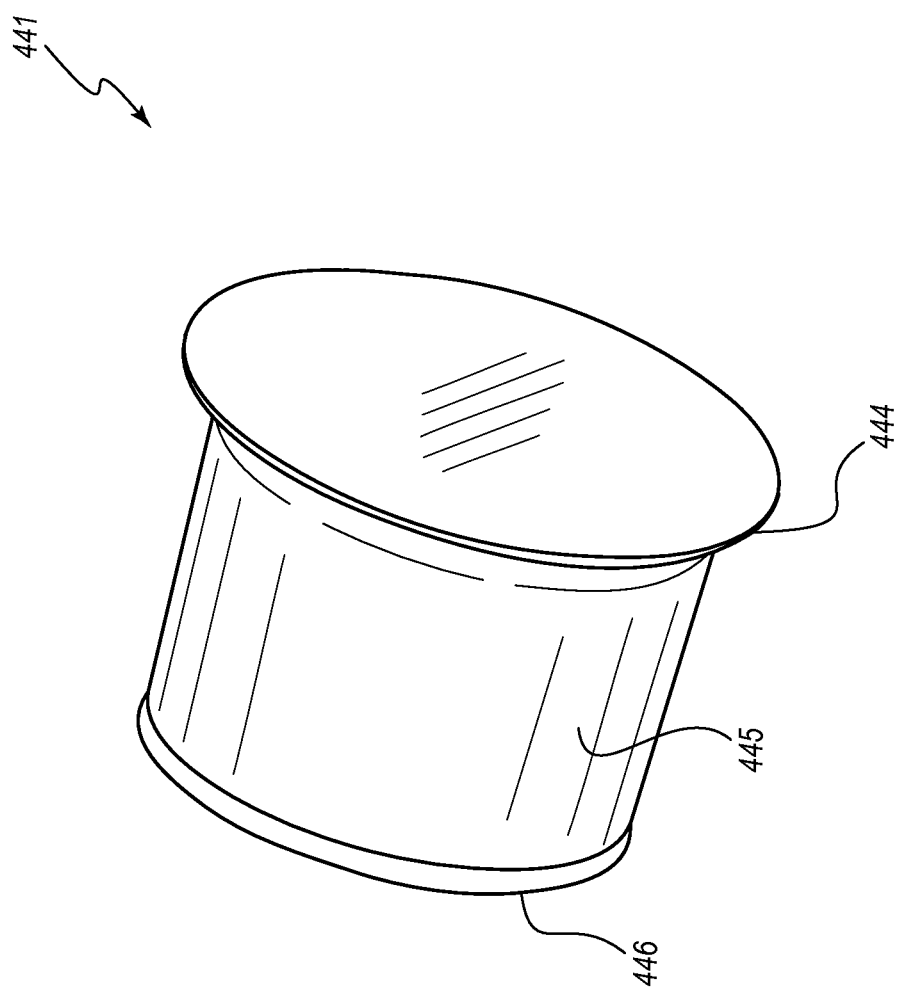
FIG. 13 is a perspective view of an embodiment of a sealing member that is compatible with the female cap of FIG. 11.
Figure 14:
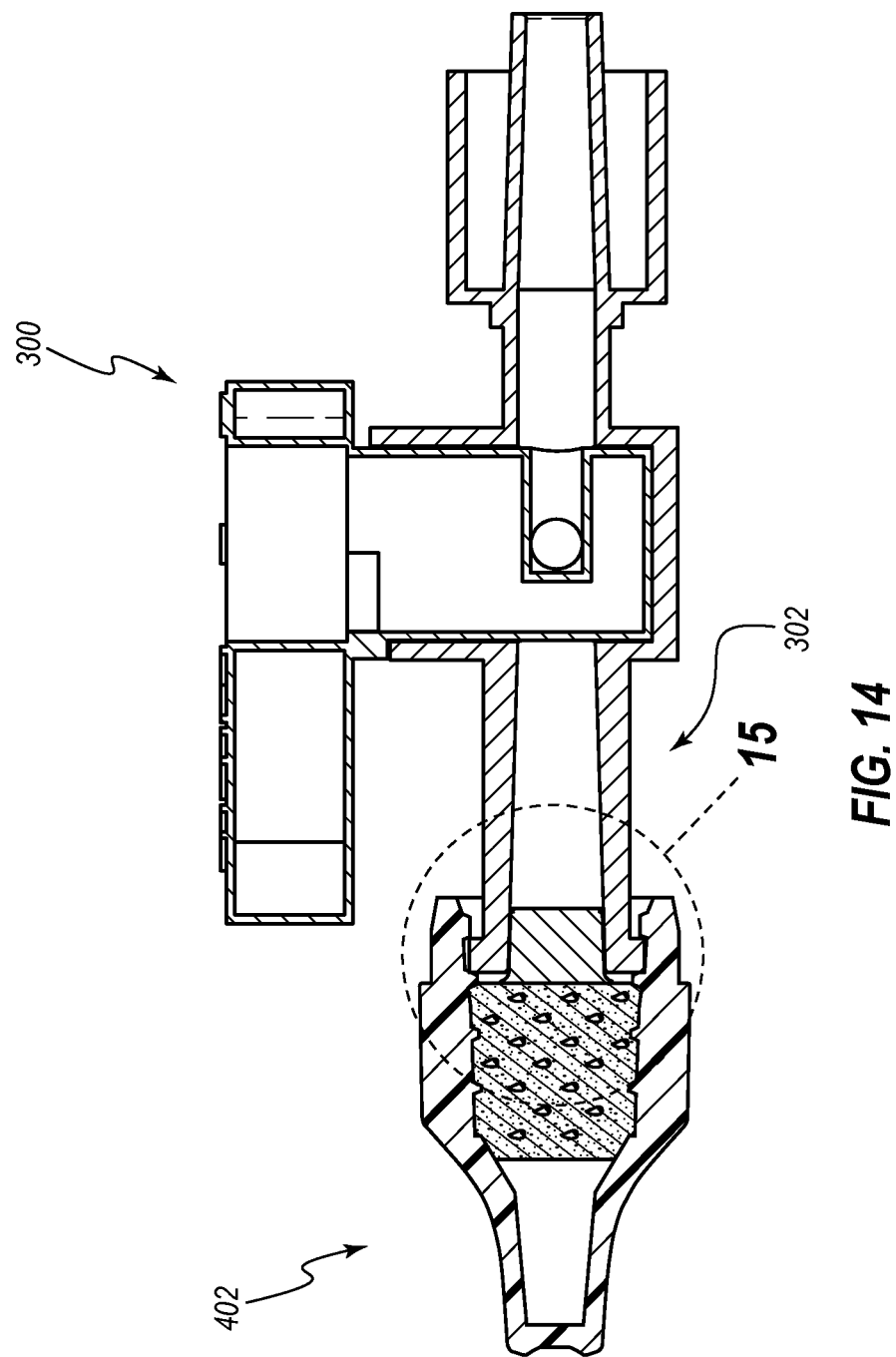
FIG. 14 is a cross-sectional view of the cap of FIG. 11 coupled with a medical connector.

As shown in FIG. 12, the female cap 402 can include a seal inhibitor 425 that resembles the seal inhibitor 125 described above. However, the seal inhibitor 425 can define a slightly different shape. In particular, the contact regions 126 and the venting regions 127 can define a castellation pattern. In other or further embodiments, the cap 402 may be devoid of a seal inhibitor 425, since, for example, certain medical connectors with which the cap 402 may be coupled may not have outwardly projecting surfaces against which a seal may be formed at the distal end of the female cap 402 (see, e.g., FIGS. 14 and 15).

Figure 15:
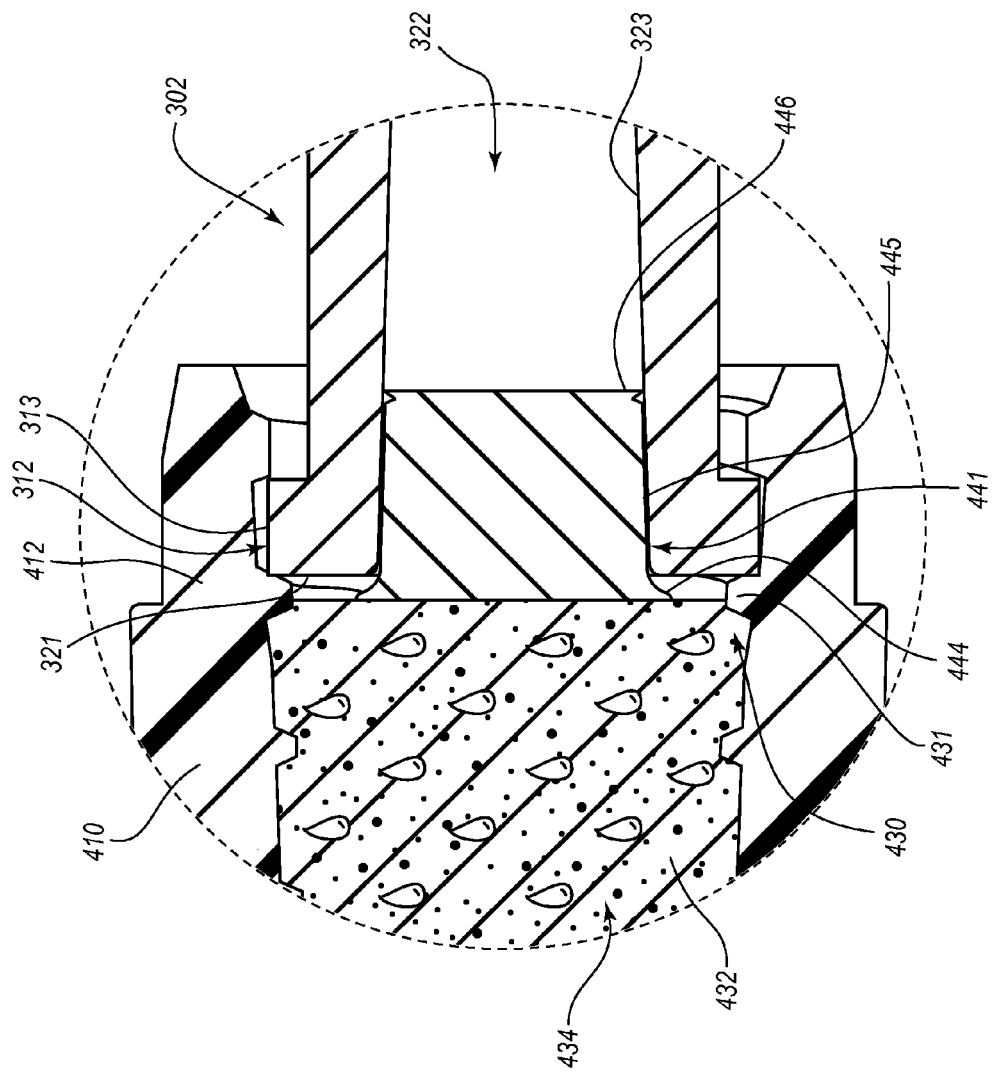
FIG. 15 is an enlarged cross-sectional view of the cap of FIG. 11 coupled with the medical connector that is taken along the view line 15-15 in FIG. 14.

With reference to FIG. 15, the cap 402 can include a support member 434 that comprises a pad 432, such as the support member 134 and pad 132 described above. With reference to FIGS. 12-15, and in particular, FIG. 15, the cap 402 can include a sealing member 441 that resembles and functions similarly to the sealing member 141 described above, but that defines a different shape. The sealing member 441 may be more plug-like than the sealing member 441, in that it can be configured to contact a greater portion of an interior surface 323 of the female connector or port 302. The sealing member 441 can include a base region 444, a tapered region 445, and a proximal flange region 446. In the illustrated embodiment, the base region 444 defines a greater maximum diameter than do the tapered region 445 and the flange region 446. The maximum diameter of the tapered region 445 can be larger than an inner diameter of the port 302 at the proximal end 321 thereof. The base region 444 may prevent direct contact with the pad 434, in some embodiments.

The tapered region 445 can be configured to form a seal along a significant length of the interior surface 323 of the port 302, which can ensure that antiseptic is not introduced into the fluid path 322. In some embodiments, the interior surface 323 of the port 302 and the tapered region 445 of the sealing member 441 each conform to standard ISO luer specifications, such that a fluid-tight seal is formed once the cap 402 has been advanced over the port 302 by a sufficient amount. In some embodiments, the proximal flange 446 may be flexible, particularly in a distal direction. The proximal flange 446 may, in further embodiments, define an outer diameter that is slightly larger than an outer diameter defined by a proximal end of the tapered region 445. The proximal flange 446 may enhance a strength of the seal formed by the sealing member 441 and/or facilitate entry of the sealing member 441 into the female lumen defined by the port 302.

Figure 16:
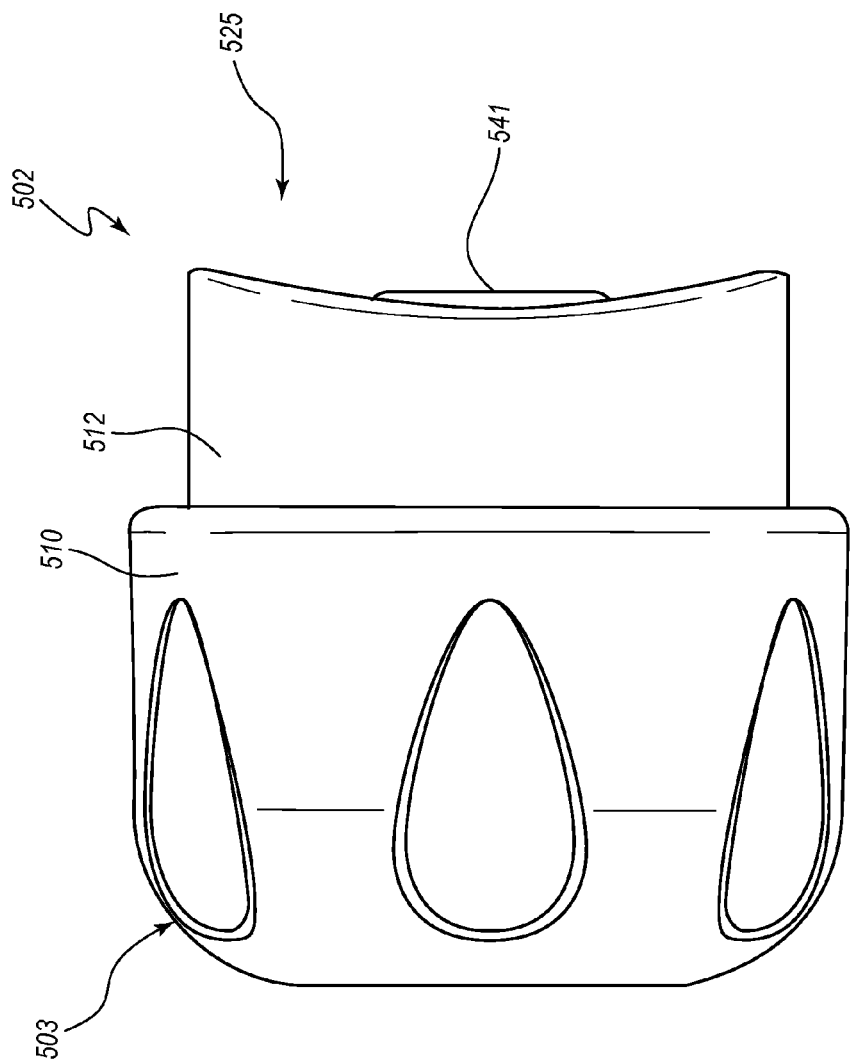
FIG. 16 is a side elevation view of another embodiment of a cap that is configured to form a seal with a medical connector.
Figure 17:
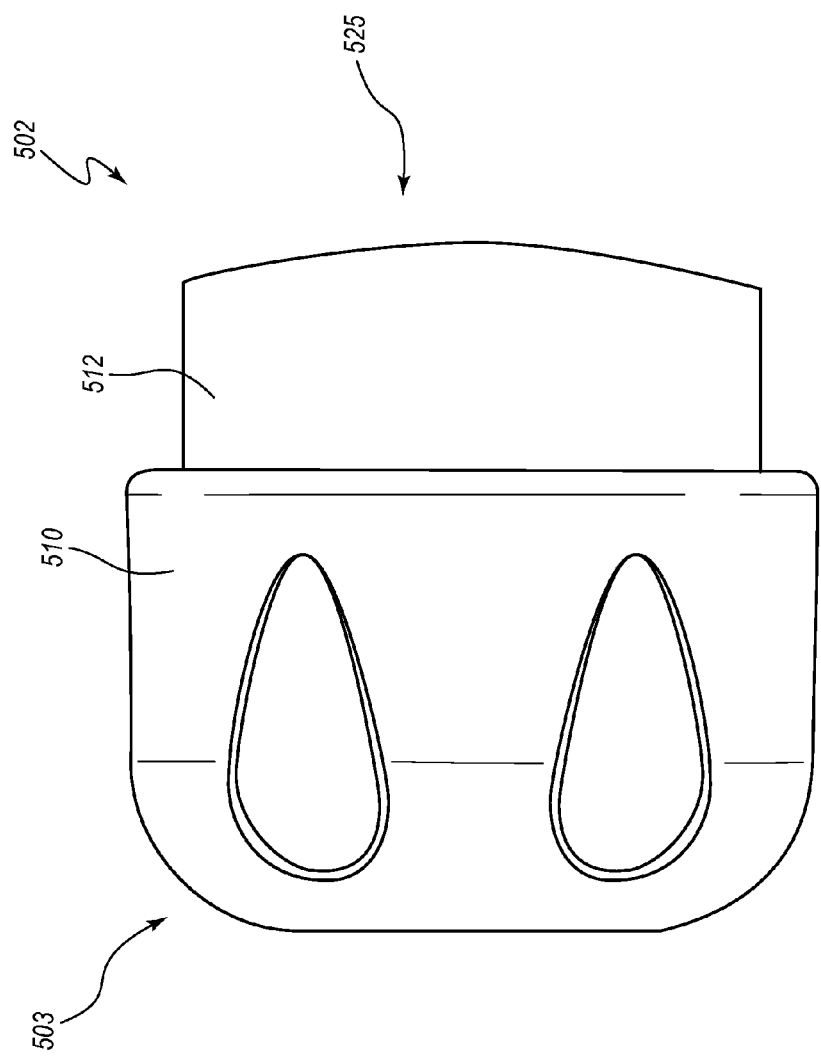
FIG. 17 is a top plan view of the cap of FIG. 16.

FIGS. 16-19B illustrate another embodiment of a female cap 502, which can be compatible with various cap assemblies disclosed herein. The cap 502 can include a housing 510 that includes a sidewall 512 and an base wall 513. As shown in FIG. 16, a distal end of the housing 510 can include gripping features 503 that are shaped differently from the gripping features 103. In the illustrated embodiment, the gripping features 503 comprise tear-shaped depressions. A proximal end of the housing can include seal inhibitors 525, which can resemble any of the seal inhibitors discussed above.

Figure 18:
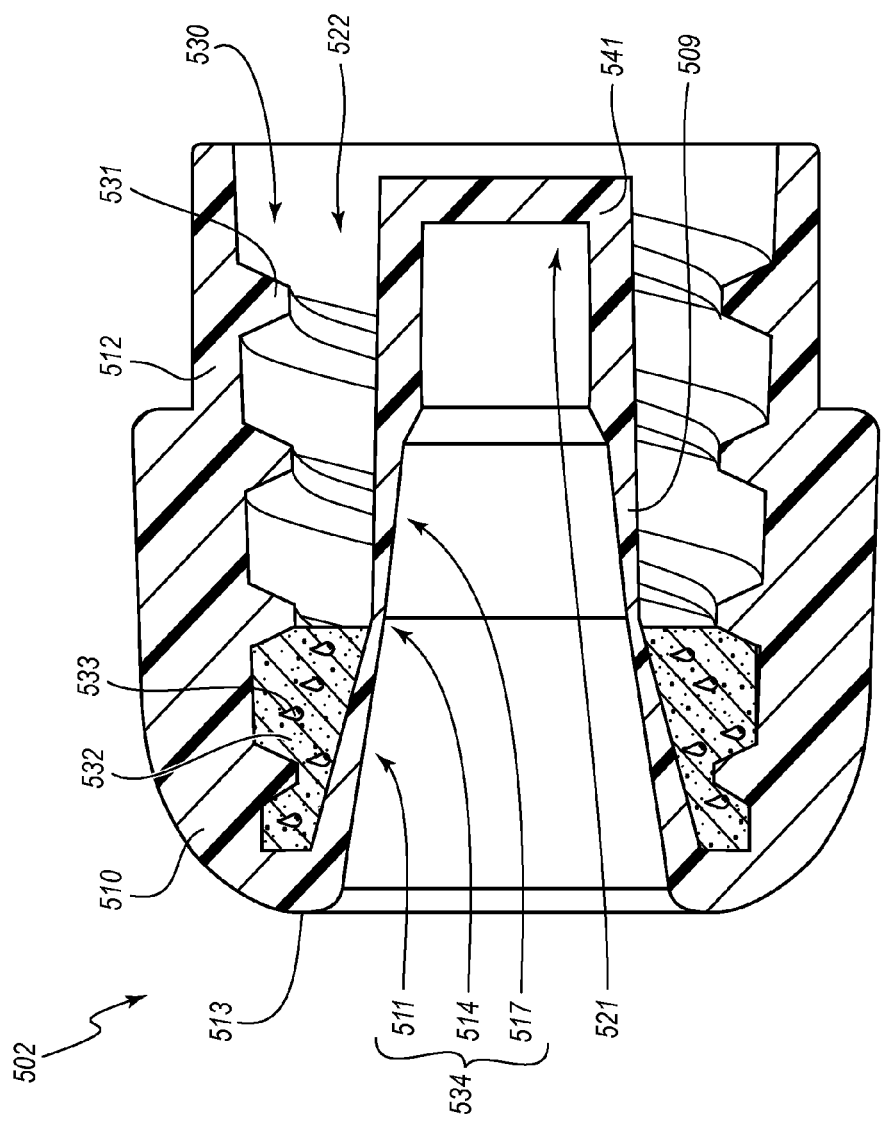
FIG. 18 is a cross-sectional view of the cap of FIG. 16.

With reference to FIG. 18, the housing 510 can further define a central post 509 that extends proximally from the base wall 513. The post 509 provide for a disinfecting chamber 522 that has a smaller volume, as compared with other female caps described above. Further, a pad 532 that is disposed at a distal end of the chamber 522 can define a substantially annular shape, and may comprise less material than certain other embodiments of pads described herein.

The post 509 can include multiple regions, which may have different or specific functions. In the illustrated embodiment, a proximal region 521 of the post 509 can be somewhat thicker than other portions thereof. The proximal region 521 can define a sealing member 541 portion of the cap 502. An outward portion of the proximal region 521 thus may be configured to plug and/or seal a female lumen of a medical connector, and thus may, in further embodiments, have a luer-shaped taper (although other configurations are also possible).

A medial region 517 of the post 509 may extend distally from the proximal region 521, and may narrow in thickness in the distal direction toward a folding, bending, crumpling, or weakened region 514. The weakened region 514 may define a minimum thickness of the post 509. In the illustrated embodiment, the weakened region 514 is a circular region that extends about a periphery of the post 509. A distal region 511 can extend distally from the weakened region 514, and can increase in thickness in the distal direction. Together, the medial region 517, the weakened region 514, and the distal region 511 can cooperate as a stress concentrator and may be configured to collapse. These regions may define a support member 534 that is configured to support the sealing member 541 sufficiently to permit the sealing member to form a seal with a medical connector, and then collapse upon application of a sufficient amount of force to permit the sealing member 541 to move distally and allow contact between the medical connector and the pad 532, as discussed hereafter. The support member 534 can be configured to collapse upon application of a predetermined amount of force thereto. In some embodiments, deformation of the support member 534 may resemble the deformation that occurs when a thin-walled aluminum can (e.g., for soft drinks) is compressed and torqued.

The support member 534 can be plastically deformable, or substantially plastically deformable, such that little restorative forces arise after the support member 534 has collapsed. In other embodiments, the collapsible support member 534 may be resiliently deformable. The post 509 may be integrally formed with the remainder of the housing 510, or it may be attached thereto. The post 509 and/or the remaining portions of the housing 510 can be formed of any suitable material. In various embodiments, the post 509 and/or the housing 510 can comprise any suitable form of injection moldable, medical grade plastic, including, for example, polypropylene, polyethylene, polycarbonate, polyurethane, ABS, thermoplastic materials, thermoplastic elastomers, etc.

Figure 19A:
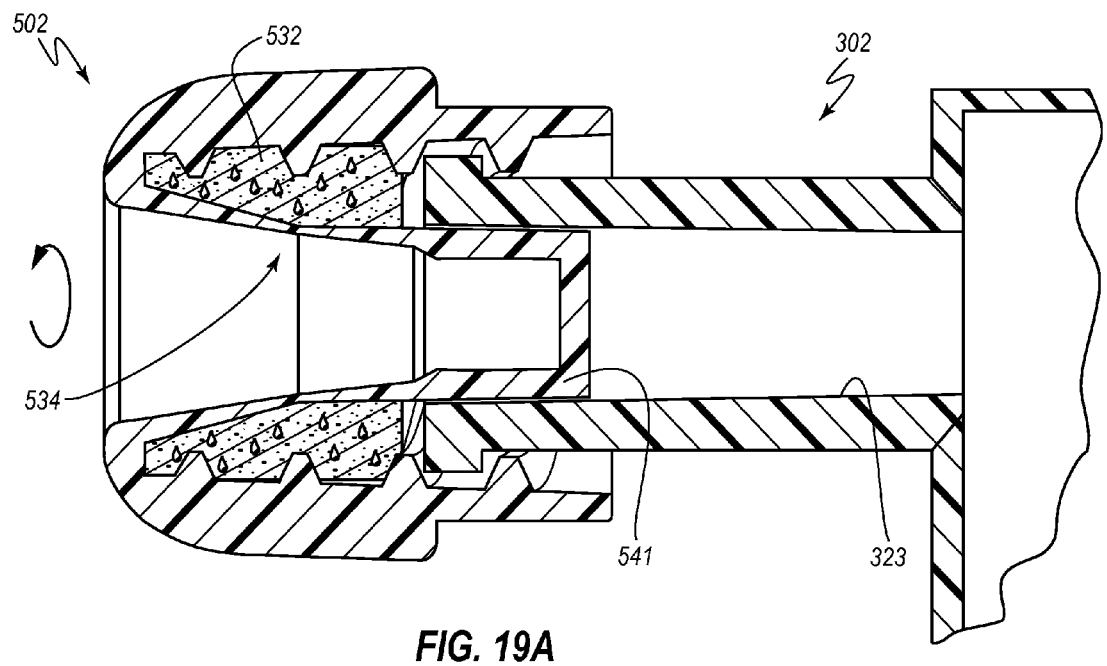
FIG. 19A is a cross-sectional view of the cap of FIG. 16 illustrating an initial stage of coupling the cap with a medical connector.

FIG. 19A depicts an early stage of a procedure for coupling the female cap 502 with a medical connector, such as the port 302. In the illustrated embodiment, connection interfaces of the cap 502 and the port 302 are used to tighten the cap 502 onto the port 302. The sealing member 541 can form a fluid-tight seal with an interior surface 323 of the port 302. A relational geometry of the sealing member 541 and the pad 532 can be such that the seal is formed before any portion of the port 302 contacts the pad 532. Accordingly, in the illustrated embodiment, a distal end of the port 302 is spaced from the pad 532 after the seal has been formed. The resistance forces to insertion of the port 302 into the cap 502 provided by the support member 534 thus can be sufficient to allow creation of the seal.

Figure 19B:
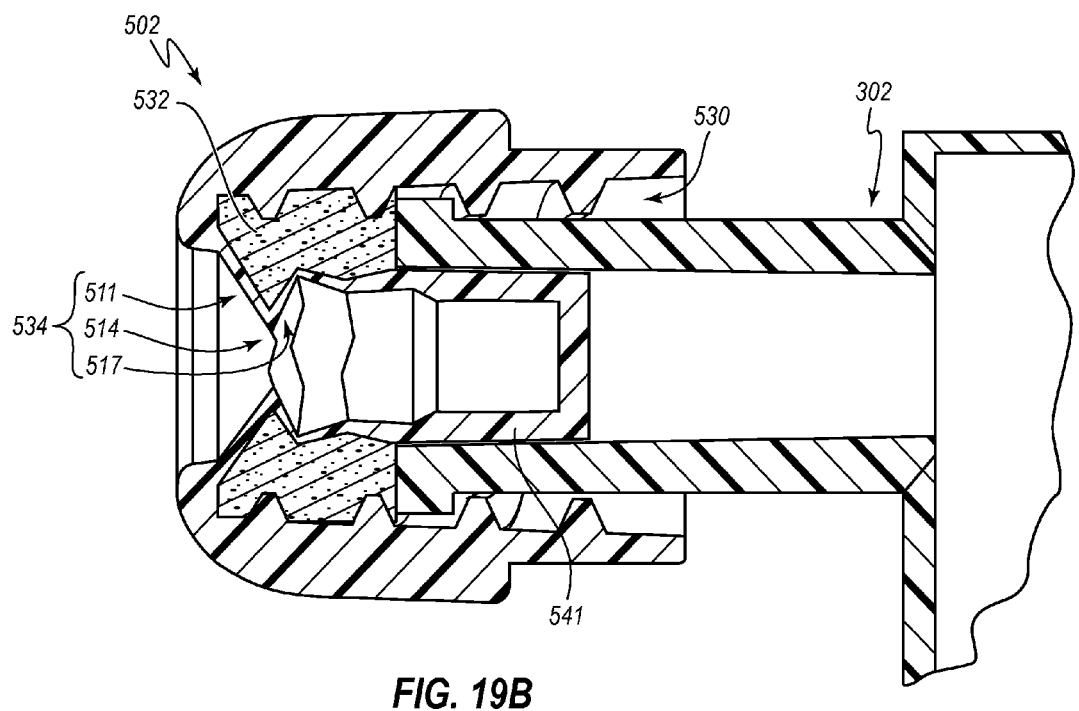
FIG. 19B is a cross-sectional view of the cap of FIG. 16 illustrating a final stage of coupling the cap with a medical connector.

FIG. 19B depicts a later stage of the coupling procedure. The port 302 has been inserted further into the cap 502 so as to compress the pad 532 and expel antiseptic therefrom. The relative orientation of the sealing member 541 and the connector 302 is relatively unchanged. However, the additional compressive forces imparted to the support member 534 as the port 302 is advanced to this position overwhelm the support member 534 and cause it to collapse. In particular, the medial region 517 and the distal region 511 fold inward about the weakened region 514.

The configuration shown in FIG. 19A can be referred to as an initial orientation of each of the sealing member 541 and the support member 534. The configuration shown in FIG. 19B can be referred to as a retracted orientation of each of the sealing member 541 and the support member 534. When in the retracted orientation, each of the sealing member 541 and the support member 534 has moved distally relative to a connection interface 530 defined by the female cap 502.

Figure 20:
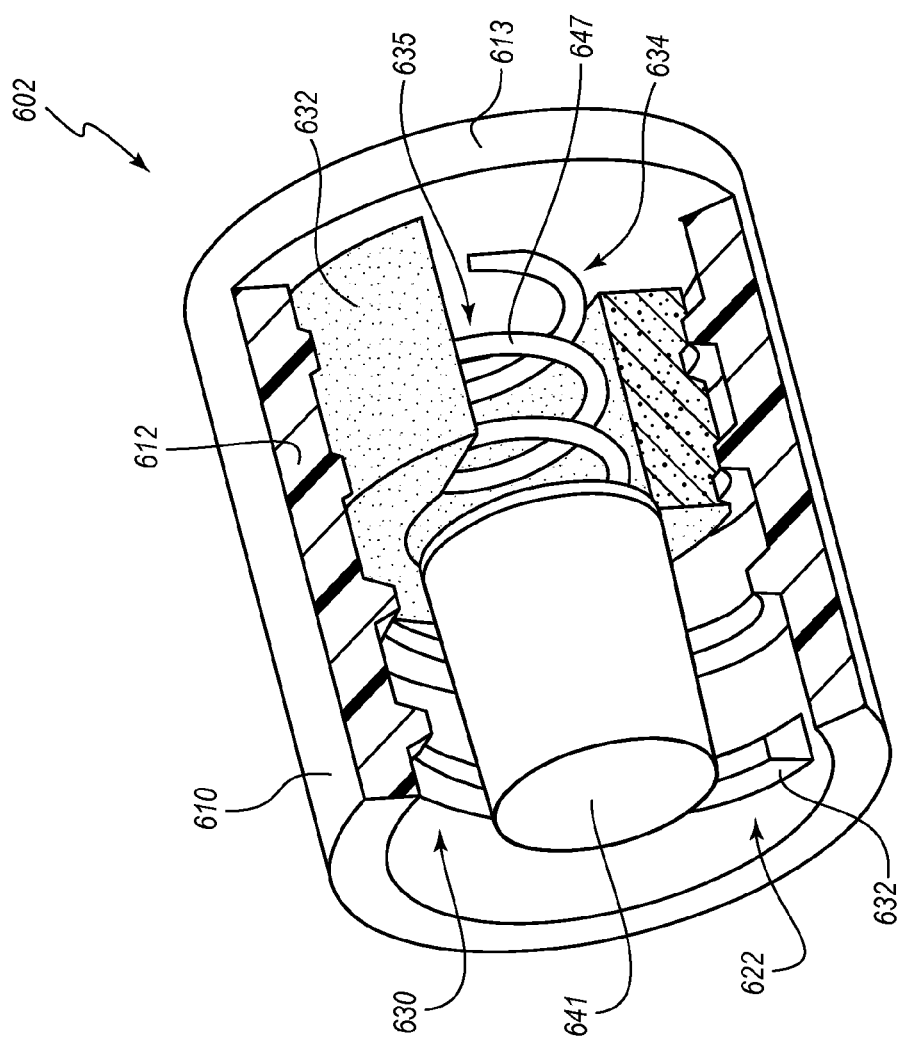
FIG. 20 is a partial cross-sectional perspective view of another embodiment of a cap that is configured to form a seal with a medical connector.

FIG. 20 illustrates another embodiment of a female cap 602, which can be compatible with various cap assemblies disclosed herein. The cap 602 can include a housing 610 that includes a sidewall 612 and an base wall 613. The sidewall 612 can define a connection interface 630 that includes inwardly directed threads 632. The sidewall 612 can also define a disinfecting chamber 622.

The cap 602 includes a sealing member 641, which can resemble other sealing members discussed herein. In the illustrated embodiment, the sealing member 641 can be configured to plug a portion of a female lumen of a medical connector. The sealing member 641 can define a substantially frustoconical shape.

The cap 602 can include a pad 632 that retains an antiseptic therein. In the illustrated embodiment, the pad 632 substantially defines an annulus, and can extend about a support member 634. In particular, the pad 632 can define a cavity 635 through which the support member 634 extends.

The support member 634 can be resiliently deformable. In the illustrated embodiment, the support member 634 comprises a coil spring 647. In other embodiments, the support member 634 can comprise one or more springs that are in forms other than helical, such as, for example, beam, leaf, conical, torsion, etc. Such springs may comprise any suitable material, such as, for example, metals and/or polymers. The spring 647 can extend between the base wall 613 of the housing 610 and the sealing member 641. In the illustrated embodiment, a distal end of the sealing member 641 is longitudinally spaced from (e.g., is positioned above) a proximal end of the pad 632.

In use, the sealing member 641 of the cap 602 forms a seal with a female lumen of a medical connector. After formation of the seal, a distal end of the medical connector can come into contact with the pad 632 so as to compress the pad 632 and expel antiseptic therefrom. This contact can also serve to swab the portion of the medical connector that contacts the pad 632. Each of the sealing member 641 and the support member 647 thus can transition from the initial orientation shown in FIG. 20 to a retracted orientation, in which the sealing member 641 and the support member 647 are closer to the base wall 613. In transitioning to the retracted orientation, at least a portion of the sealing member can travel through a portion of the cavity 635 defined by the pad 632. Upon decoupling of the cap 602 from the medical connector, the support member 647 can return to its initial orientation, and can also urge the sealing member 641 back to the initial orientation.

Figure 21:
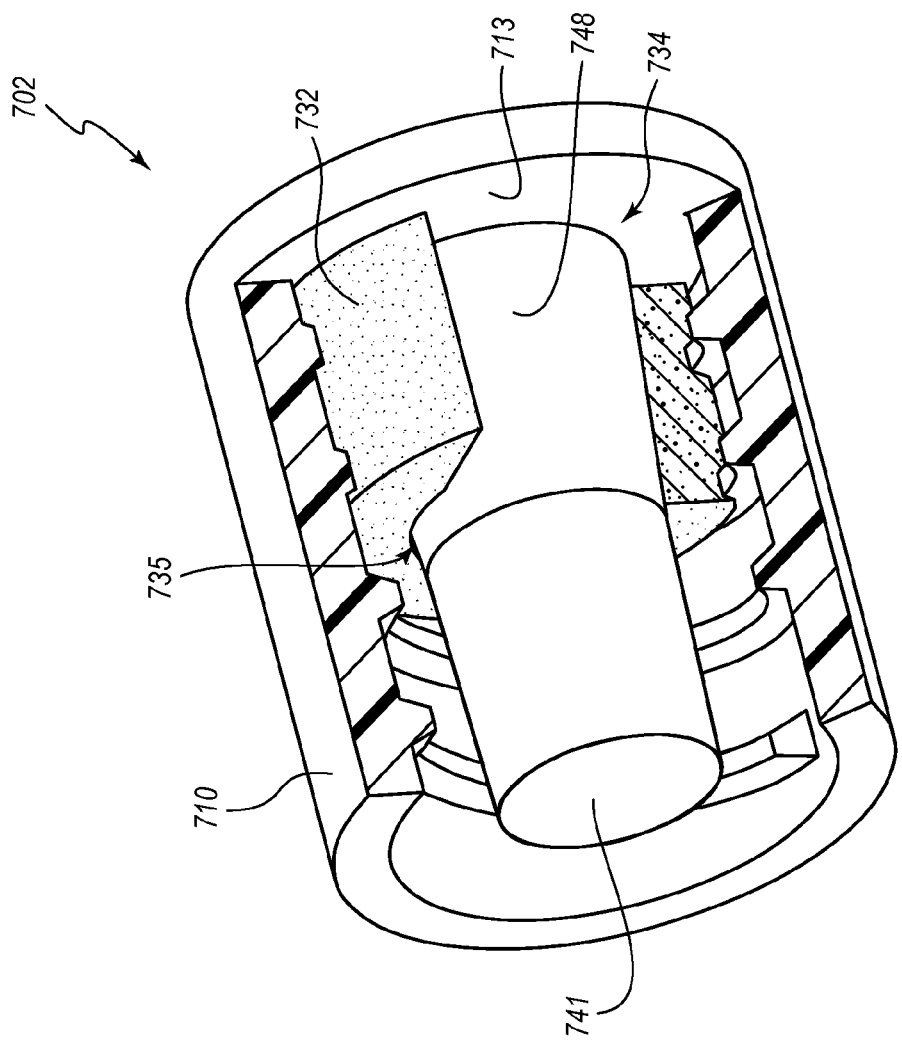
FIG. 21 is a partial cross-sectional perspective view of another embodiment of a cap that is configured to form a seal with a medical connector.

FIG. 21 illustrates another embodiment of a female cap 702, which can be compatible with various cap assemblies disclosed herein, and can particularly resemble the cap 602. The cap 702 can include a housing 710 with a base wall 713 such as the housing 610 and base wall 613, a pad 732 such as the pad 632, and a sealing member 741 such as the sealing member 641. However, the cap 702 can include a support member 734 that comprises a compressible pad 748. In some embodiments, the pad 748 is plastically deformable, and in other embodiments, the pad is resiliently deformable. The resiliently deformable embodiments can operate substantially the same as support member 647 described above.

Figure 22:
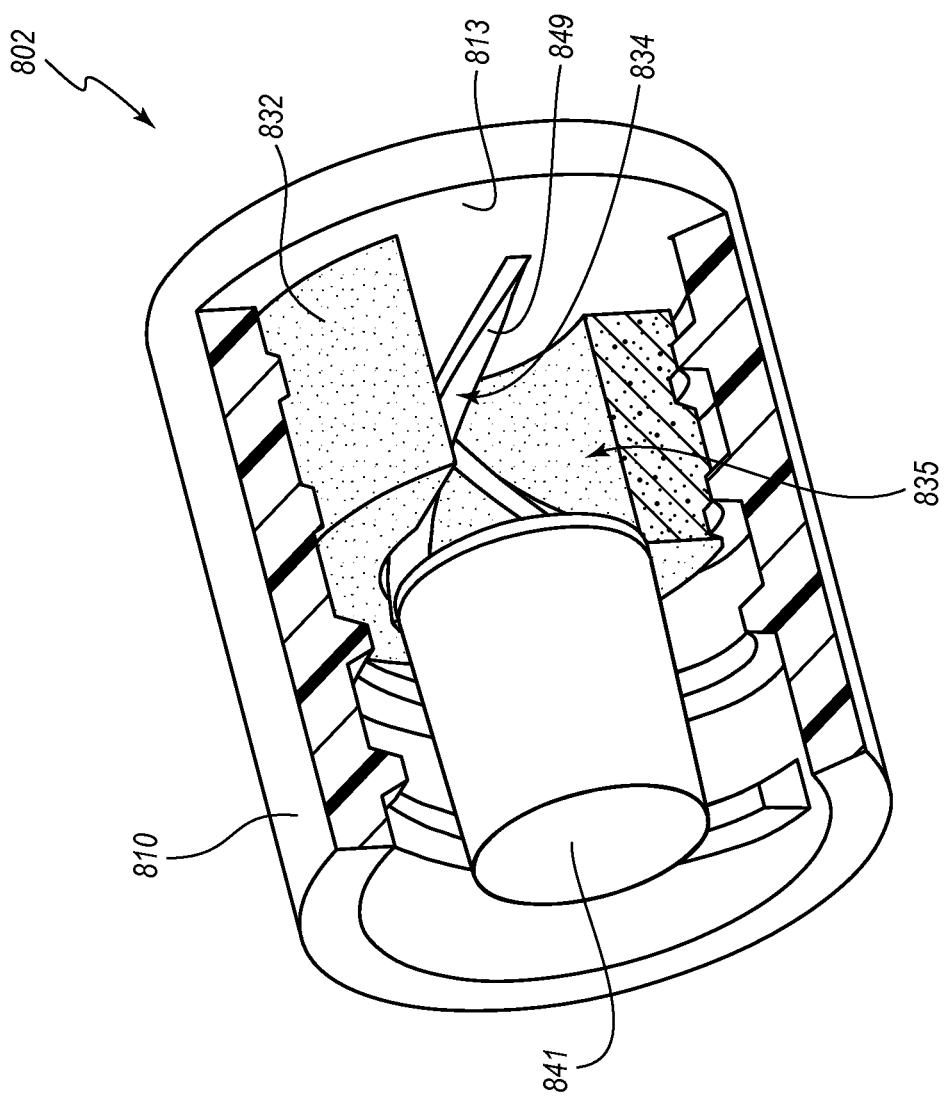
FIG. 22 is a partial cross-sectional perspective view of another embodiment of a cap that is configured to form a seal with a medical connector.

FIG. 22 illustrates another embodiment of a female cap 802, which can be compatible with various cap assemblies disclosed herein, and can particularly resemble the cap 602. The cap 802 can include a housing 810 with a base wall 813 such as the housing 610 and base wall 613, a pad 832 such as the pad 832, and a sealing member 841 such as the sealing member 641. However, the cap 802 can include a support member 834 that comprises one or more collapsible extensions 849. In some embodiments, the extensions comprise molded parts, which may be integral with the housing 810 or attached thereto. In some embodiments, the extensions 849 are plastically deformable, and in other embodiments, they are resiliently deformable. The resiliently deformable embodiments can operate substantially the same as support member 647 described above.

Figure 23A:
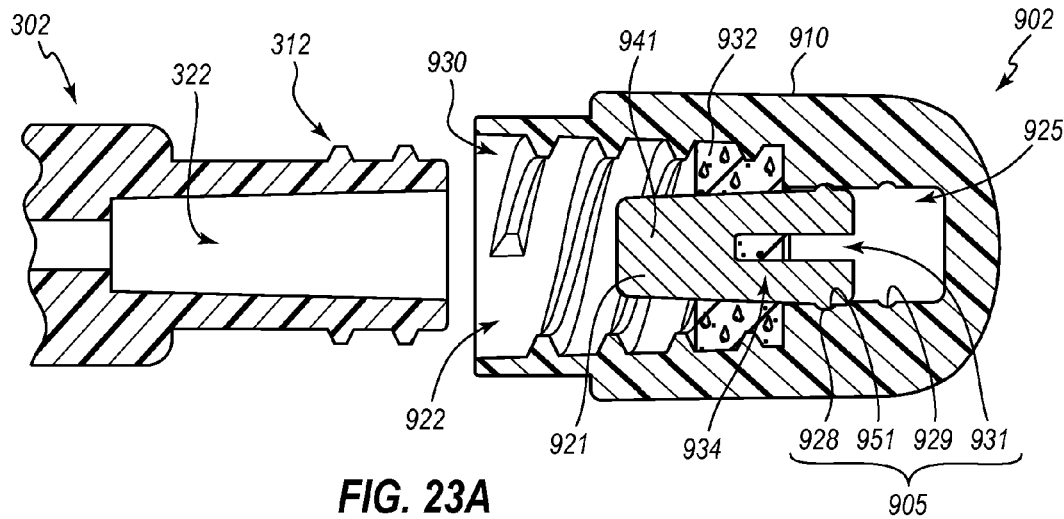
FIGS. 23A-23C are cross-sectional views illustrating various stages of coupling another embodiment of a cap with a medical connector.
Figure 23B:
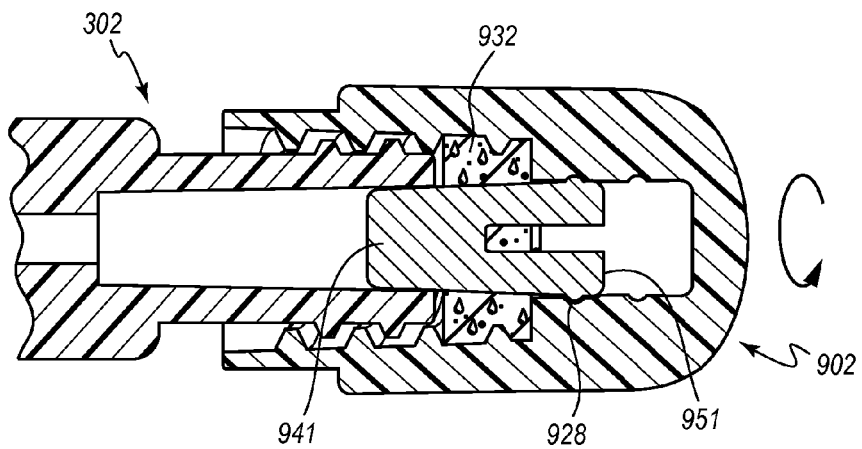
Figure 23C:
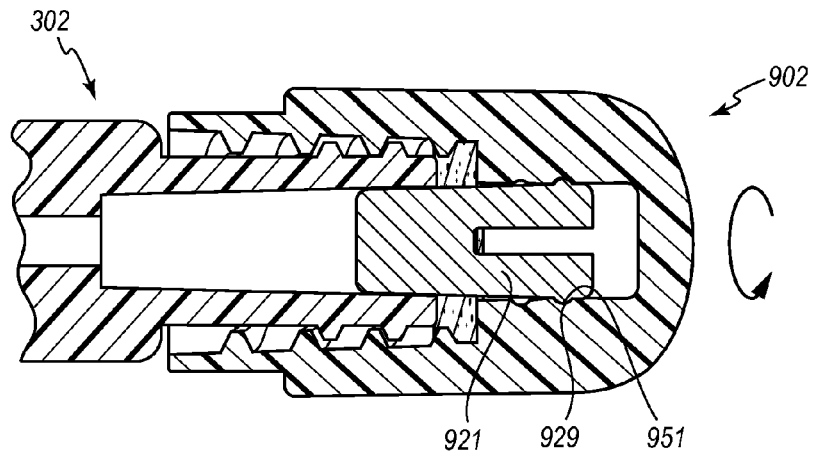

FIGS. 23A-23C illustrate another embodiment of a female cap 902 that is configured for connection to a medical connector 302, which includes a connection interface 312 and defines a female lumen 322. The cap 902 can include a housing 910 that defines a connection interface 930, a disinfecting chamber 922, and a distal cavity or chamber extension 925. The chamber extension 925 can extend the disinfecting chamber 922 distally. A sidewall of the chamber extension 925 can include locking features, such as detents or, in the illustrated embodiment, grooves 928, 929. In particular, a proximal groove 928 and a distal groove 929 are defined, although more grooves are possible. The grooves may extend about at least a portion of a periphery of the chamber extension 925.

The cap 902 can include a shuttle or plug 921 that is configured to translate within the chamber extension 925. An annular pad 932 can extend about that plug 921. The plug 921 can include a sealing member 941 and a support member 934. In the illustrated embodiment, the sealing member 941 and support member 934 are integrally formed from the same piece of material. Other arrangements are also possible.

In some embodiments, the support member 934 can include a relief groove 931, which can allow for radial compression of the support member 934 and may permit the support member 934 to be under tension when it is within the chamber extension 925. The support member 934 can define locking features that are complementary to those of the chamber extension 925. For example, in the illustrated embodiment, the support member 934 defines outwardly projecting detents 951 that are sized to be received within either of the grooves 928, 929. Together, the detents 951 and grooves 928, 929 can operate as a locking system or latching system 905. The relief groove 931 can also contribute to operation of the latching system 905. Other suitable latching system arrangements are also contemplated.

The plug 921 can be configured to transition from the initial position shown in FIGS. 23A and 23B to the retracted position shown in FIG. 23C. In particular, with reference to FIG. 23B, the connector 302 can form a fluid tight seal with the sealing member 941. Interaction between the proximal groove 928 and the detent 951 can be sufficiently strong to maintain the sealing member 941 in its initial orientation so as to form the seal with the connector 302. A distal end of the connector 302 may be spaced from the pad 932 at this point, so as to prevent antiseptic from entering into the lumen 322 prior to creation of the seal.

Upon further advancement of the connector 302 into the cap 902, the forces on the plug 921 can be sufficient to cause radial compression of the support member 934 so as to move the detent 951 to the distal groove 929. In some embodiments, the detent 951/groove 929 pairing can maintain the plug 921 in the retracted position when the medical connector 302 is removed from the cap 902.

Figure 24:
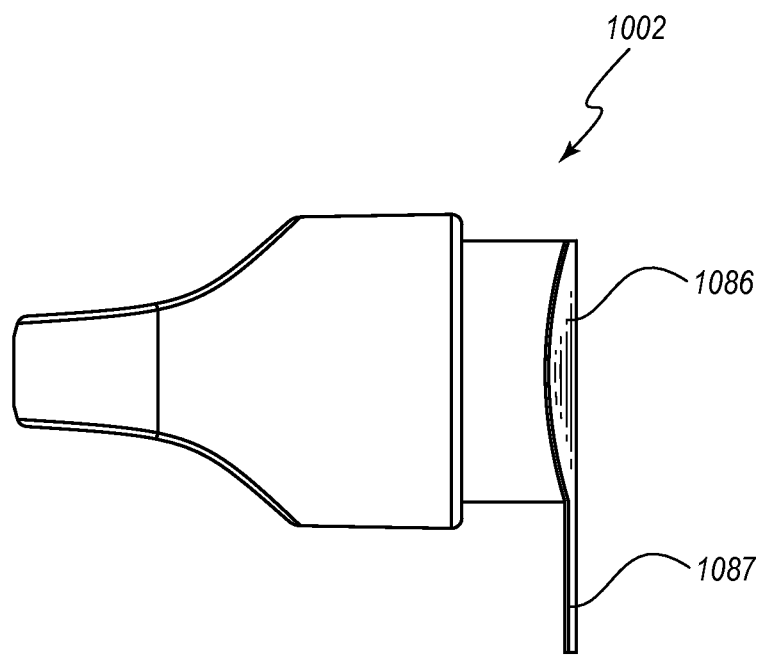
FIG. 24 is a side elevation view of another embodiment of a cap that is configured to form a seal with a medical connector.

In some embodiments, a cap 1002 can be packaged independently of another cap when in a pre-use state, such that it may not be part of an assembly. For example, as shown in FIG. 24, in some embodiments, a removable cover 1086 may be secured to a proximal end of a cap 1002 in any suitable manner, such as, for example, via an adhesive. Preferably, the cover 1086 can be readily removed by a practitioner. The cover 1086 may include a graspable tab 1087 to aid in the removal thereof. The removable cover 1086 can be formed of any suitable material, such as, for example, an impervious pliable material (e.g., foil, plastic, metallized-surface mylar). Examples of suitable covers are illustrated in U.S. patent application Ser. No. 12/917,336, titled DISINFECTING CAPS AND SYSTEMS AND ASSOCIATED METHODS, filed Nov. 1, 2010.

Figure 25:
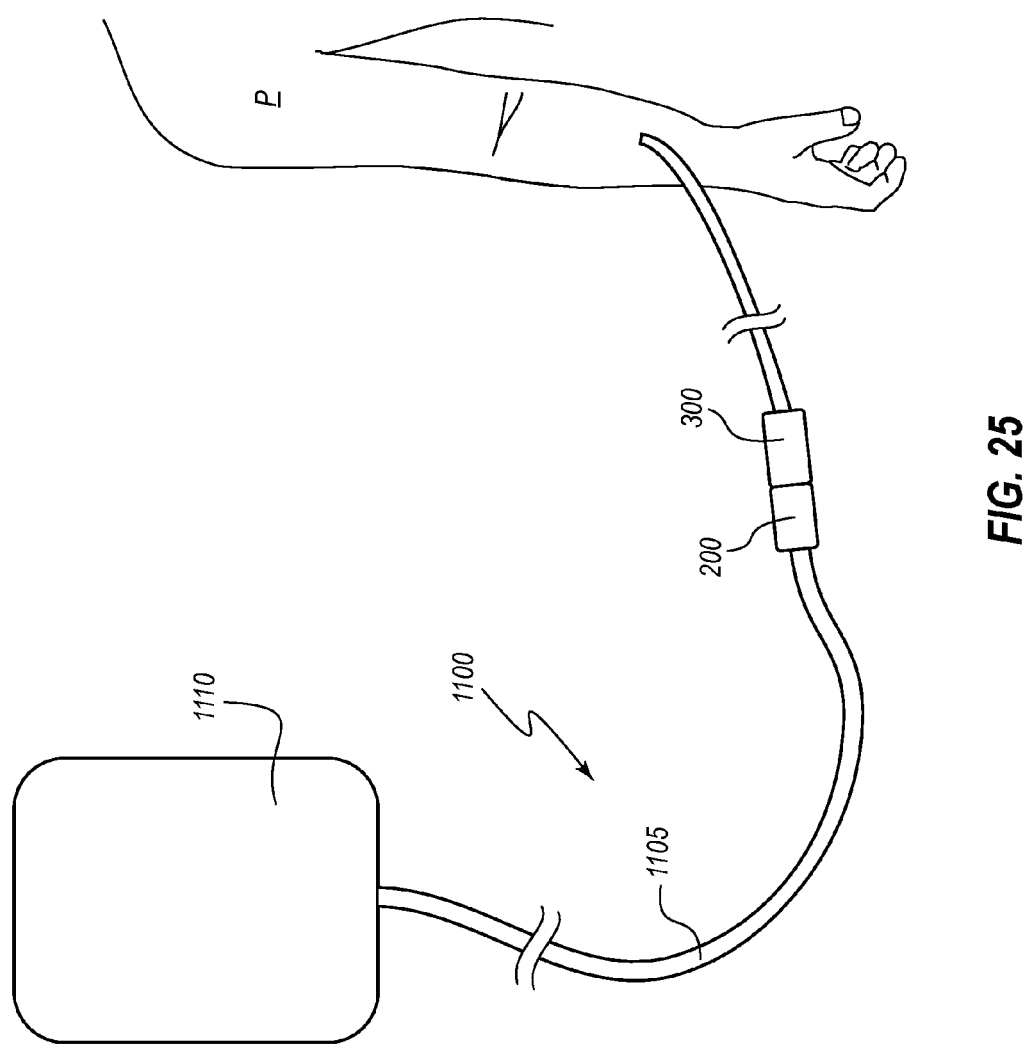
FIG. 25 is a perspective view of a fluid line that includes a coupled set of connectors that are amenable to being coupled with male and female caps, respectively.

FIG. 25 illustrates an example of medical connectors 200, 300 for which caps disclosed herein may be used. Any suitable variety of medical connectors 200, 300 is possible, such as, for example, luer lock connectors. The connectors 200, 300 are associated with a fluid pathway 1100, such as a fluid line 1105 of any suitable variety, which may be coupled with an IV bag 1110 or other suitable fluid delivery system. Commonly, the fluid pathway 1200 can be used to intermittently administer medications to a patient P.

In the illustrated embodiment, the connector 300 of the fluid pathway 1100, which communicates fluids with a patient's blood stream, may be selectively disconnected from the connector 200. One or more of the connectors 200, 300 may be connected to other connectors (not shown), such as a connector associated with a central line. The medical connectors 200, 300 may be connected and disconnected at various times, and may remain disconnected for several minutes or hours. Medical connector caps disclosed herein can be used to cover and protect the various medical connectors 200, 300 while the connectors are separated from one another.

The foregoing disclosure recites various embodiments that include caps that are configured to disinfect medical connectors. Certain of such caps can include a housing that defines a connection interface and that defines a chamber in which an antiseptic is retained. Illustrative examples of means for sealing a fluid path of a medical connector include the sealing members 141, 190, 441, 541, 641, 741, 841, and 941. Illustrative examples of means for supporting the means for sealing a fluid path include the supporting members 134, 176, 434, 534, 634, 734, 834, and 934.

It will be understood by those having skill in the art that many changes may be made to the details of the above-described embodiments without departing from the underlying principles presented herein. For example, any suitable combination of features of the various embodiments of assemblies described above is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

It should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Recitation in the claims of the term "first" with respect to a feature or element does not necessarily imply the existence of a second or additional such feature or element. Elements recited in means-plus-function format are intended to be construed in accordance with 35 U.S.C. §112¶6. It will be apparent to those having skill in the art that changes may be made to the details of the above-described embodiments without departing from the underlying principles of the invention.

What is claimed is:

1. A female-disinfecting cap for applying an antiseptic agent to an open female luer hub, the cap comprising:
 a cap body defining a chamber having only a single opening, a back wall opposite the opening and a sidewall, the chamber having means for engaging threads of an externally threaded female luer hub having an open lumen, the means being disposed near the opening,
 an absorbent material for holding an antiseptic agent disposed in the chamber;
 a sealing component disposed within the chamber configured to sealingly engage with the lumen when the female luer hub is received into the chamber to prevent flow of the antiseptic agent into the lumen of the female luer hub while permitting the flow of the antiseptic agent past the sealing member to outwardly facing surfaces of the female luer hub, the sealing component traveling within the chamber when engaged with the female luer hub in a motion concordant with the motion of the female luer hub; and
 a biasing component disposed between the back wall of the chamber and the sealing member, the biasing component biasing the sealing component towards the opening of the chamber.

2. A cap according to claim 1, wherein the cap body further comprises a gripping portion.

3. A cap according to claim 1, further comprising a cover disposed over the opening of the chamber.

4. A cap according to claim 3, wherein the cover comprise an impervious pliable material.

5. A cap according to claim 4, wherein the impervious pliable material comprise a foil.

6. A cap according to claim 1, wherein the chamber comprises at least one frustoconical sidewall.

7. A cap according to claim 1, wherein a perimeter of the sidewall decreases from the opening to the interior of the chamber with a first slope.

8. A cap according to claim 7, wherein the perimeter of the sidewall defines a second slope different from the first slope.

9. A cap according to claim 7, wherein the second slope is disposed distally in the chamber and is steeper than the first slope.

10. A cap according to claim 1, wherein an outer diameter of the sealing component conforms with ISO luer specification.

11. A cap according to claim 1, wherein the means for engaging threads of the externally threaded female luer hub is a thread.

12. A cap according to claim 1, further comprising a recess on an outer surface of the cap near the opening for receiving a sleeve.

13. A cap according to claim 12, wherein the recess has a geometry that facilitates removal of the sleeve by a twisting motion.

14. A cap according to claim 1, wherein an outer diameter of the sealing component is smaller than an outer diameter of the biasing component.

15. A cap according to claim 1, wherein a proximal portion of the sealing member is a cone.

16. A cap according to claim 1, wherein the biasing component forms an integral part with the back wall of the chamber and the sealing component.

17. A cap according to claim 16, wherein the biasing component and the sealing component have a differing wall thickness.

18. A cap according to claim 1, wherein the biasing component is a spring.

19. A female-disinfecting cap for applying an antiseptic agent to an open female luer hub, the cap comprising:
- a cap body defining a chamber having only a single opening, a back wall opposite the opening and a sidewall, the chamber having means for engaging threads of an externally threaded female luer hub having an open lumen, the means being disposed near the opening,
- an absorbent material for holding an antiseptic agent disposed in the chamber;
- a sealing component disposed within the chamber configured to sealingly engage with the lumen when the female luer hub is received into the chamber to prevent flow of the antiseptic agent into the lumen of the female luer hub while permitting the flow of the antiseptic agent past the sealing member to outwardly facing surfaces of the female luer hub, the sealing component traveling within the chamber when engaged with the female luer hub in a motion concordant with the motion of the female luer hub; and
- a collapsible component disposed between the back wall of the chamber and the sealing member.

20. A cap according to claim 19 wherein the collapsible component forms an integral part with the back wall of the chamber and the sealing member.

21. A female-disinfecting cap for applying an antiseptic agent to an open female luer hub, the cap comprising:
- a cap body defining a chamber having only a single opening, a back wall opposite the opening and a sidewall, the chamber having means for engaging threads of an externally threaded female luer hub having an open lumen, the means being disposed near the opening,
- an absorbent material for holding an antiseptic agent disposed in the chamber;
- a sealing component disposed within the chamber configured to sealingly engage with the lumen when the female luer hub is received into the chamber to prevent flow of the antiseptic agent into the lumen of the female luer hub while permitting the flow of the antiseptic agent past the sealing member to outwardly facing surfaces of the female luer hub, the sealing member being integral with the body of the cap at an end distal to the opening, the sealing component having a variable wall thickness between a distal end a proximal end, wherein the proximal end is closer to the single opening of the chamber than the distal end and the wall thickness decreases from the proximalend towards the interior of the chamber.

\* \* \* \* \*

UNITED STATES PATENT AND TRADEMARK OFFICE
CERTIFICATE OF CORRECTION

| | | |
|---|---|---|
| PATENT NO. | : 8,523,831 B2 | Page 1 of 1 |
| APPLICATION NO. | : 12/957263 | |
| DATED | : September 3, 2013 | |
| INVENTOR(S) | : Donald D. Solomon et al. | |

It is certified that error appears in the above-identified patent and that said Letters Patent is hereby corrected as shown below:

In the Claims:

In Column 24, Line 62, Claim 9
Change "A cap according to claim 7,"
To "A cap according to claim 8,"

In Column 26, Line 34, Claim 21
Change "the proximalend towards the interior of the chamber"
To "the proximal end towards the interior of the chamber"

Signed and Sealed this
Eleventh Day of February, 2014

Michelle K. Lee
*Deputy Director of the United States Patent and Trademark Office*